(12) United States Patent
Pruckner et al.

(10) Patent No.: US 10,653,399 B2
(45) Date of Patent: *May 19, 2020

(54) MEDICAL OR DENTAL INSTRUMENT WITH A TEMPERATURE-MEASURING DEVICE

(71) Applicant: W&H Dentalwerk Bürmoos GmbH, Bürmoos (AT)

(72) Inventors: Christian Pruckner, Vienna (AT); Karlheinz Eder, Michaelbeuern (AT); Johann Grosslhuber, Anthering (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 55 days.

This patent is subject to a terminal disclaimer.

(21) Appl. No.: 15/346,572

(22) Filed: Nov. 8, 2016

(65) Prior Publication Data

US 2017/0049424 A1 Feb. 23, 2017

Related U.S. Application Data

(63) Continuation of application No. 14/080,745, filed on Nov. 14, 2013, now Pat. No. 9,526,585, which is a (Continued)

(30) Foreign Application Priority Data

| May 19, 2011 | (EP) | ................................. | 11166638 |
| Oct. 24, 2011 | (EP) | ................................. | 11186293 |
| Dec. 23, 2011 | (EP) | ................................. | 11195549 |

(51) Int. Cl.
  *A61B 17/00* (2006.01)
  *A01J 5/04* (2006.01)
  (Continued)

(52) U.S. Cl.
  CPC .............. *A61B 17/00* (2013.01); *A61B 90/06* (2016.02); *A61C 1/0007* (2013.01);
  (Continued)

(58) Field of Classification Search
  CPC .................... A61B 17/00; A61B 90/06; A61B 2017/00084; A61B 2562/271;
  (Continued)

(56) References Cited

U.S. PATENT DOCUMENTS

| 2,642,742 A | 6/1953 | Heidenwolf |
| 4,509,029 A | 4/1985 | Bradley |
| (Continued) | | |

FOREIGN PATENT DOCUMENTS

| EP | 0178567 | 4/1986 |
| EP | 1982668 | 10/2008 |
| (Continued) | | |

OTHER PUBLICATIONS

International Search Report for PCT/EP2012/059288 (dated Feb. 7, 2013).

(Continued)

*Primary Examiner* — Cris L. Rodriguez
*Assistant Examiner* — Hao D Mai
(74) *Attorney, Agent, or Firm* — Klarquist Sparkman, LLP

(57) ABSTRACT

Medical or dental instruments, preferably handpieces, can have different temperature-measuring devices for measuring the temperature in the instrument or of at least a part of the instrument. The temperature-measuring devices can be designed, for example, to measure the temperature contactlessly by detection of electromagnetic radiation or to measure the temperature of an interior of the instrument that can be heated by a heat source. The temperature-measuring devices may be designed, for example, as electrical tem- (Continued)

perature-measuring devices or may have a magnetic material whose magnetic property is a function of temperature and/or has a temperature-dependent course. The temperature-measuring device may have, for example, an electrical switching device and a signal device wherein the signal device is switched at least between a first signal condition and a second signal condition when a temperature limit value is reached or exceeded or is underrun.

23 Claims, 10 Drawing Sheets

Related U.S. Application Data continuation of application No. PCT/EP2012/059228, filed on May 18, 2012.

(51) Int. Cl.

| | |
|---|---|
| A61C 1/00 | (2006.01) |
| G01J 5/10 | (2006.01) |
| G01K 7/38 | (2006.01) |
| G01K 13/00 | (2006.01) |
| A61C 19/04 | (2006.01) |
| A61B 90/00 | (2016.01) |
| G01K 7/02 | (2006.01) |
| H01H 37/58 | (2006.01) |
| G01J 5/04 | (2006.01) |

(52) U.S. Cl.
CPC ............ *A61C 1/0015* (2013.01); *A61C 19/04* (2013.01); *G01J 5/041* (2013.01); *G01J 5/10* (2013.01); *G01K 7/02* (2013.01); *G01K 7/38* (2013.01); *G01K 13/00* (2013.01); *A61B 2017/00084* (2013.01); *A61B 2562/0271* (2013.01); *H01H 37/585* (2013.01)

(58) Field of Classification Search
CPC ..... A61C 1/0007; A61C 1/0015; A61C 19/04; G01J 5/041; G01J 5/10; G01K 7/02; G01K 7/38; G01K 13/00; H01H 37/585
See application file for complete search history.

(56) References Cited

U.S. PATENT DOCUMENTS

| | | |
|---|---|---|
| 5,123,839 A | 6/1992 | West |
| 5,179,291 A | 1/1993 | Nishikawa et al. |
| 5,268,622 A | 12/1993 | Philipp |
| 5,516,285 A | 5/1996 | Yacker |
| 5,941,702 A | 8/1999 | Sharp et al. |
| 6,470,222 B1 | 10/2002 | Davidson et al. |
| 6,503,081 B1 | 1/2003 | Feine |
| 6,752,816 B2 | 6/2004 | Culp et al. |
| 6,786,897 B2 | 9/2004 | Mc Ie et al. |
| 7,422,582 B2 | 9/2008 | Malackowski et al. |
| 8,204,612 B2 | 6/2012 | Feine et al. |
| 2004/0150504 A1 | 8/2004 | Nicholson |
| 2004/0185412 A1 | 9/2004 | Feine |
| 2005/0031239 A1 | 2/2005 | Aoki et al. |
| 2006/0074405 A1 | 4/2006 | Malackowski et al. |
| 2007/0015112 A1 | 1/2007 | Hochman et al. |
| 2008/0014550 A1 | 1/2008 | Jones et al. |
| 2008/0234964 A1 | 9/2008 | Miyasaka |
| 2009/0259244 A1 | 10/2009 | Shimizu |
| 2009/0322541 A1 | 12/2009 | Jones et al. |
| 2010/0036535 A1 | 2/2010 | Feine et al. |
| 2010/0055642 A1 | 3/2010 | Rothenwaender et al. |
| 2011/0236851 A1 | 9/2011 | Muller et al. |
| 2012/0107762 A1 | 5/2012 | Sauter et al. |
| 2014/0120496 A1 | 5/2014 | Rothenwaender et al. |
| 2014/0134565 A1 | 5/2014 | Kunisada |

FOREIGN PATENT DOCUMENTS

| | | |
|---|---|---|
| EP | 2215981 | 8/2010 |
| GB | 2438877 | 12/2007 |
| JP | 03047249 | 2/1991 |
| JP | H0347249 A | 2/1991 |
| JP | 03123234 | 12/1991 |
| JP | 04332391 | 11/1992 |
| JP | 06280771 | 10/1994 |
| JP | 07255197 | 10/1995 |
| JP | 2007195993 | 8/2007 |
| JP | 2009254821 A | 11/2009 |
| JP | 2010051797 A | 3/2010 |
| WO | WO2006/110670 | 10/2006 |
| WO | WO2009/072035 | 6/2009 |
| WO | WO2009/138324 | 11/2009 |

OTHER PUBLICATIONS

Dyson et al., "Flow and free running speed characterization of dental air turbine handpieces," Journal of Dentistry, 27(7):465-477 (Sep. 1999); 13 pages.
D21, "Electrical measurement of temperature with thermocouples and resistance thermometers;" 28 pages.
D22, "Praxis of temperature measurement:" 14 pages.

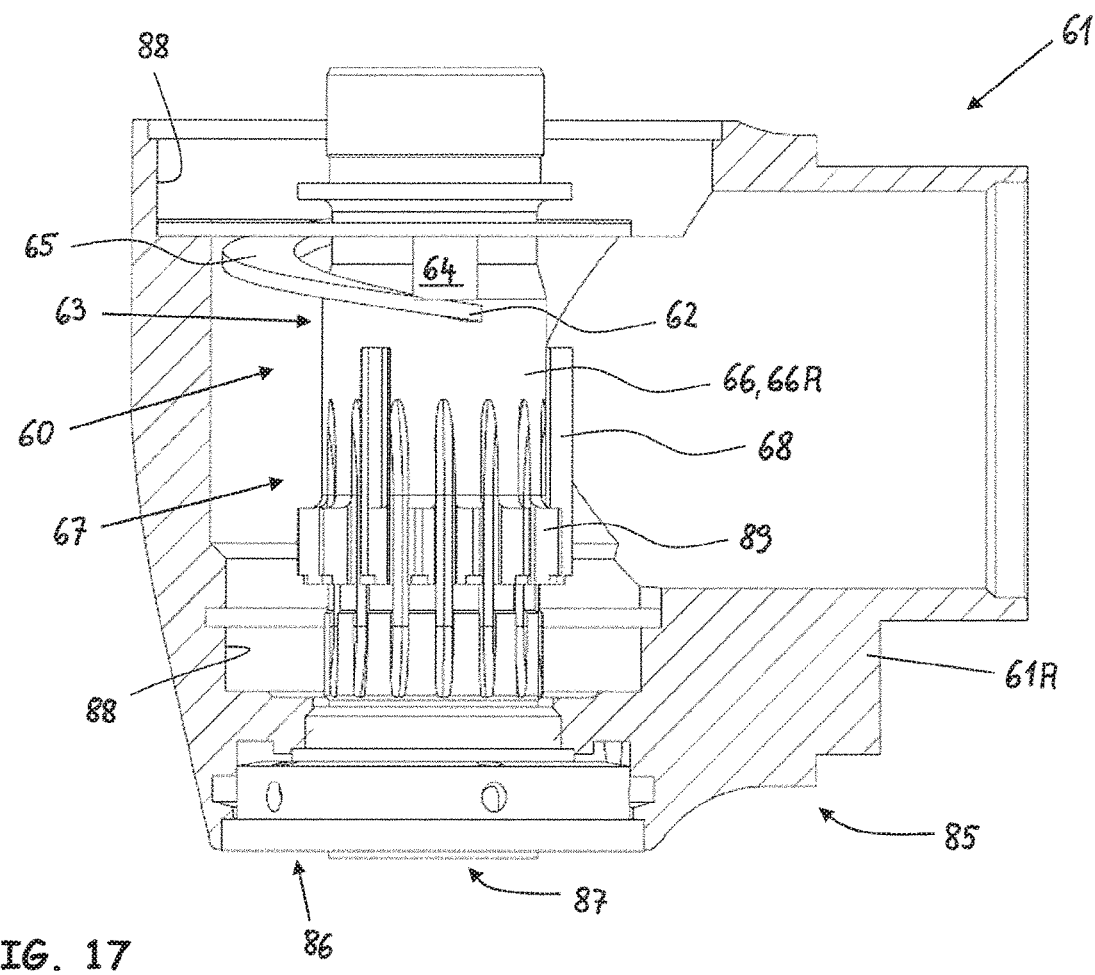
FIG. 17
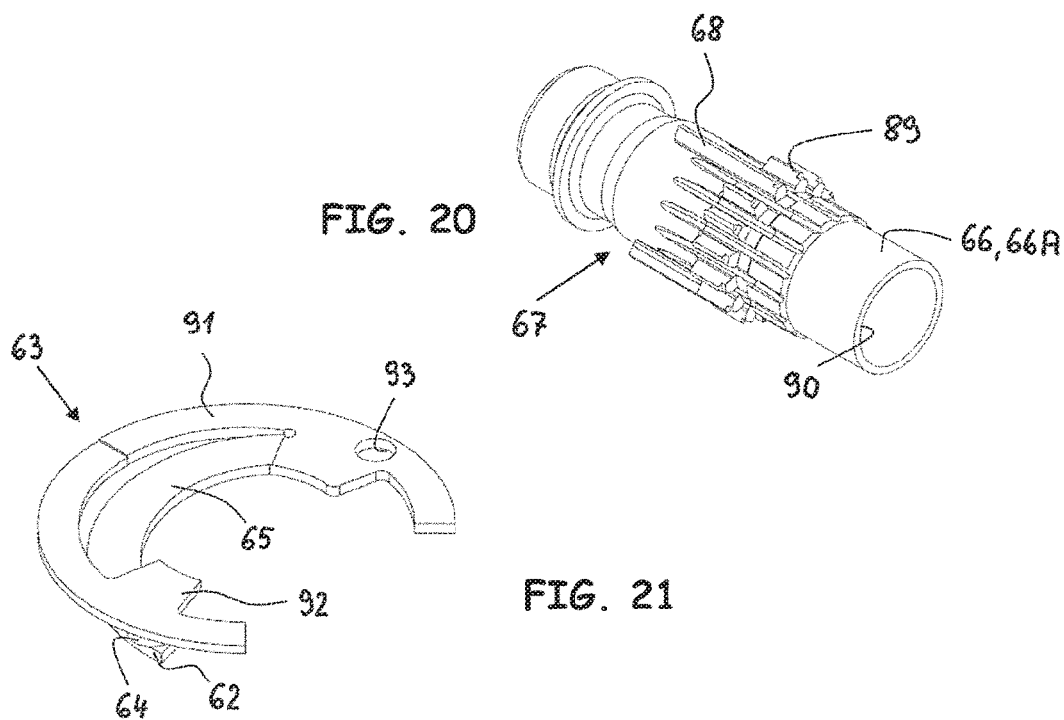
FIG. 20
FIG. 21

MEDICAL OR DENTAL INSTRUMENT WITH A TEMPERATURE-MEASURING DEVICE

CROSS REFERENCE TO RELATED APPLICATION

The present application is a continuation of U.S. patent application Ser. No. 14/080,745, filed Nov. 14, 2013, which is a continuation of International Patent Application No. PCT/EP2012/059228, filed May 18, 2012, and designating the United States, which was published in German and claims priority from European Patent Application Nos. 11166638.4, filed May 19, 2011, and 11186293.4, filed Oct. 24, 2011 and from European Patent Application No. 11195549.8, filed Dec. 23, 2011, now abandoned, which are incorporated herein by reference.

BACKGROUND

Field

The present invention relates to a medical or dental instrument, preferably a handpiece with a temperature-measuring device for measuring the temperature of the instrument or of a part of the instrument.

Description of Prior Art

Such a handpiece is known from U.S. Pat. No. 6,786,897 B2 for example. The handpiece is provided with a releasable cap or with a dye or lacquer containing a temperature-sensitive or thermochromic dye indicating a temperature change by changing colors.

The disadvantage of this handpiece is that, among other things, the thermochromic dye reflects the change in temperature only inaccurately and with a time lag, and the temperature is measured and displayed exclusively on the components of the handpiece, where the thermochromic dye has been applied.

US Patent Application 2009/0322541 A1 discloses a handpiece, in which the head housing is provided with a skeleton-shaped or rib-shaped girdle having a central band and lateral detection bands protruding away from it, with the temperature sensors, among other things, being provided on these bands. The lateral detection bands transmit the heat released by the different heat sources to the temperature sensors by means of thermal conduction.

The disadvantage of this handpiece consists among other things again of the delayed and imprecise temperature measurement because of the thermal conduction via the detection bands and the fact that the temperature measurement is limited to certain regions or components of the handpiece due to the arrangement of the detection bands.

SUMMARY

One object of the present invention is therefore to create a medical or dental handpiece and a corresponding method having an alternative temperature-measuring device for measuring the temperature of the handpiece or of a part of the handpiece, which in particular does not have one or more of the aforementioned disadvantages.

According to one embodiment, a medical or dental handpiece is provided, comprising: an outer shell, a drive device for inducing movement of a tool that can be connected to the handpiece and a temperature-measuring device for measuring the temperature of the handpiece or of a part of the handpiece, wherein the temperature-measuring device is designed to measure the temperature of the handpiece or of a part of the handpiece, for example, one or more components of the handpiece or an interior of the handpiece without contact by detection of electromagnetic radiation, in particular thermal radiation.

The advantage of a temperature measurement which measures the temperature in a contact-freely by detecting electromagnetic radiation consists among other things of the fact that the temperature measurement is performed very rapidly and independently, in particular at a spatially separate location from the heat source. Because of the spatial separation, measurement of the temperature of movable or moving components of the handpiece is preferably possible without coming in contact with them, thus preventing wear on the temperature sensor in particular. Due to the detection of electromagnetic radiation the measurement of the temperature is also independent of external influences, e.g., convection.

According to one embodiment, the temperature-measuring device is arranged and/or designed to receive electromagnetic radiation from several heat sources arranged in or on the outer shell of the handpiece and/or radiation from the outer shell in particular to determine an average temperature value of the several heat sources and/or of the outer shell. The temperature-measuring device, which measures the temperature in a contact-free manner by detecting electromagnetic radiation is preferably arranged and/or designed so that it determines an average temperature value, in particular an average temperature value of multiple components and/or heat sources of the handpiece and/or of a volume of space surrounding the temperature-measuring device, for example, a partial volume of the handpiece, in particular the handpiece head of the handpiece, in which a tool holder is provided for the tool that can be connected to the handpiece. The volume of space or the partial volume mentioned above whose average temperature can be measured is in particular greater than the volume of the temperature-measuring device or of the sensor of the temperature-measuring device, preferably many times greater than the volume of the temperature-measuring device or of the sensor of the temperature-measuring device.

A temperature-measuring device, which receives electromagnetic radiation from several heat sources or which determines an average temperature value is arranged, for example, between the several heat sources and/or components and/or has multiple electromagnetic radiation-receiving side faces, in particular electromagnetic radiation-receiving side faces pointing in different directions to receive electromagnetic radiation or thermal radiation from different directions.

According to one embodiment, several heat sources are provided in or on the handpiece, wherein one heat source in particular heats the handpiece or parts of the handpiece to a greater extent than another heat source, or wherein in particular one heat source emits more heat or thermal radiation than another heat source. For example, two bearings, in particular roller bearings, are provided in the handpiece or in the handpiece head, a first bearing being hotter than a second bearing because of a defect or because of soiling. The temperature-measuring device, which measures the temperature by detection of electromagnetic radiation contact-freely, is preferably arranged and/or designed in such a way that it measures a temperature value, in particular a temperature of the handpiece or of a part of the handpiece, which is influenced by the several heat sources. The temperature-measuring device is preferably arranged and/or designed so that it measures an average temperature value of the handpiece or of a part of the handpiece or of an interior of the handpiece, which results from the thermal emissions of the several heat sources or which is comprised of the heat emissions of the several heat sources. The temperature-measuring device thus advantageously does not measure exclusively or not primarily the temperature of a certain component.

The temperature-measuring device, which measures the temperature by detection of electromagnetic radiation contact-freely, is preferably arranged and/or designed, so that it measures a temperature value, in particular a temperature value of the handpiece or of a part of the handpiece or of an interior of the handpiece, preferably an average temperature value, which is influenced by one or more components of the handpiece, which are not designed as a (primary or direct) heat source, but instead can be heated by a heat source provided in the handpiece, for example, immovable components, which are connected to a heat source and are heated by it, for example, by thermal conduction or convection. The temperature-measuring device, which measures the temperature by detection of electromagnetic radiation in a contact-freely, is especially preferably arranged and/or designed so that it measures a temperature value, preferably an average temperature value, which is influenced by at least one heat source and at least one component of the handpiece, which is not designed as a heat source, but instead can be heated by a heat source provided in the handpiece.

The heat sources mentioned above may also include other components of the handpiece in addition to the aforementioned bearings, in particular any components of the hand piece that move in relation to one another, preferably movable and stationary components that contact one another, for example, a tool holder and a tool-releasing device of the handpiece or parts of the tool holder and of the tool-releasing device or a rotor of a motor or a generator or the outer shell of the handpiece and a component of the handpiece that is movable in relation thereto. A heat source may also be formed by a component, that can be supplied with electric energy such as, for example, a lighting device, an electric motor, in particular its coils, an electric or electronic circuit, a sensor or detector, etc. This list of possible heat sources is not complete and is given only as an example, and it applies accordingly to all other embodiments that are described herein.

The temperature-measuring device, which is designed to measure the temperature of the handpiece or of a part of the handpiece by detection of electromagnetic radiation contact-freely, is preferably arranged in the handpiece or in the interior of the outer shell of the handpiece so that a particularly rapid, direct and precise measurement is ensured.

According to one embodiment, the at least one heat source arranged in the outer shell of the handpiece comprises an electromagnetic radiation-emitting surface which is at a distance away from a surface of the temperature-measuring device that receives the electromagnetic radiation of the heat source. Due to this spatial separation, it is possible advantageously in particular to measure the temperatures of several heat sources and/or components that are connected to a heat source and are heated by it and/or to measure an average temperature value of the handpiece or of a part of the handpiece or of an interior of the handpiece, which results from the thermal emissions of the heat sources and/or of the components.

According to other embodiments, the temperature-measuring device, which is designed to measure the temperature of the handpiece or of a part of the handpiece by detection of electromagnetic radiation contact-freely comprises a pyrometer or an infrared sensor, these being designed in particular to detect electromagnetic radiation in a range from approximately 5 μm to approximately 20 μm. Alternatively, the temperature-measuring device has an optical conductor for electromagnetic radiation, in particular a fiber rod, whose scattering or refractive index is varied on the basis of changes in temperature.

A radiation conductor may preferably be provided on the pyrometer or on the infrared sensor, this radiation conductor being designed to conduct thermal radiation, in particular infrared radiation to the pyrometer or to the infrared sensor. This is advantageous in particular when the pyrometer or the infrared sensor cannot be positioned at the location where the temperature measurement is desired.

According to an alternative embodiment, a medical or dental handpiece is provided, comprising a hollow outer shell having an interior, a drive device for inducing movement of a tool that can be connected to the handpiece, at least one heat source arranged in the outer shell of the handpiece, heating the interior by releasing heat into the interior, and a temperature-measuring device, which is designed to measure the temperature of the interior of the handpiece that can be heated by at least one heat source.

One advantage of this handpiece is that the temperature-measuring device thus does not measure exclusively or primarily the temperature of a certain component, but instead an average temperature value can preferably be determined by means of the temperature-measuring device, in particular in the presence of several heat sources. Thus several heat sources in particular can be monitored advantageously by a smaller number of temperature-measuring devices, preferably several heat sources can be monitored by a single temperature-measuring device. The several heat sources deliver at least some of their heat to the interior of the handpiece, preferably into a partial volume of the handpiece, in particular into the handpiece head of the handpiece in which a tool holder is provided for the tool that can be connected to the handpiece. The partial volume and/or the interior mentioned above whose average temperature can be measured is in particular larger than the volume of the temperature-measuring device or of the sensor of the temperature-measuring device, preferably many times larger than the volume of the temperature-measuring device or of the sensor of the temperature-measuring device.

The interior of the handpiece is preferably formed by a volume containing a fluid, in particular air, which separates components of the handpiece from one another, the temperature-measuring device being provided in the volume. The at least one heat source delivers its heat into this volume. Alternatively or additionally, the temperature-measuring device is situated at a distance from the at least one heat source. Both of these measures increase the independence of the temperature measurement of the at least one heat source or facilitate the determination of an average temperature value.

The temperature-measuring device, which is designed to measure the temperature of the interior that can be heated by at least one heat source, comprises, for example, a pyrometer or an infrared sensor which is designed in particular to detect electromagnetic radiation in the range of approximately 5 μm to approximately 20 μm or an optical conductor for electromagnetic radiation, in particular a fiber rod whose scattering or refractive index varies on the basis of temperature changes, or an electrical temperature-measuring device, for example, a thermocouple or a temperature-measuring device comprising a material whose electric resistance or dynamic resistance is variable as a function of the temperature.

According to another alternative embodiment, a medical or dental handpiece is provided, comprising an outer shell, a drive device for inducing movement of a tool that can be connected to the handpiece and a temperature-measuring device for measuring the temperature of the handpiece or of a part of the handpiece, the temperature-measuring device being designed as an electrical temperature-measuring device.

One advantage of an electrical temperature-measuring device is, among other things, the precise and rapid determination of the temperature value.

According to a first embodiment, the electrical temperature-measuring device has at least one thermocouple which is designed to provide a thermoelectric voltage signal for the measurement of the temperature. The advantage of a thermocouple lies in particular in its simple design and its sturdiness, in particular with respect to external influences which occur during cleaning or sterilization of the handpiece for example. An evaluation unit assigned to the thermocouple is preferably provided, this unit being designed to determine a temperature value from the thermoelectric voltage signal of the thermocouple.

The term "thermocouple" refers to a device that converts heat into electric energy by thermoelectric energy. A thermocouple in particular has two different electrically conductive materials joined together at one end, in particular metals or metal wires to be able to perform temperature measurements. A thermocouple thus preferably has a bimetallic thermocontact. A temperature difference at the ends of the metals or metal wires generates an electric charge separation or a thermoelectric voltage because of the Seebeck effect within the two metals. This electric potential difference is approximately proportional to the temperature difference at the ends of the metals. To be able to determine the absolute temperature on the metals or wire ends, additional measures must be taken, for example, measuring the ambient temperature to which the temperature difference at the ends of the metals is added. Since the design and function of a thermocouple are known, they need not be discussed further here.

The at least one thermocouple preferably comprises two electrically conductive materials, in particular a metal or a metal wire, for example, steel, copper, a copper-nickel alloy (constantan) or other alloys containing nickel, chromium, iron or copper, for example.

The at least one thermocouple is preferably arranged in an interior of the handpiece, wherein the interior is formed by a volume which contains a fluid, in particular air, and which separates components of the handpiece from one another. The at least one thermocouple thus advantageously measures in particular the temperature of the interior and/or the (average) temperature of several heat sources, which deliver heat into the interior and/or an average temperature value, in particular an average temperature value of multiple components and/or heat sources of the handpiece and/or of a volume surrounding the temperature-measuring device, for example, a partial volume of the handpiece.

Alternatively, the at least one thermocouple is provided on a component of the handpiece, in particular on a heat source or on a heat-emitting component, wherein the component of the handpiece on which the thermocouple is provided preferably comprises a material which is part of the thermocouple or of the thermocouple component. The temperature of this component can be determined advantageously in particular due to the fact that the thermocouple is provided on this component of the handpiece. The design size of the thermocouple can be reduced due to the use of a material of the component on which the thermocouple is arranged as part of the thermocouple or the thermocouple component and in particular if it is a larger component, for example, the outer shell of the handpiece, the contacting of the thermocouple which transmits the thermoelectric voltage signal may be arranged at a distance from the actual thermocouple component (i.e., the contact point or area of contact of the two materials of the thermocouple), thereby simplifying the arrangement of the thermocouple and/or the contacts and lines for deriving the thermoelectric voltage signal in the constricted interior of the handpiece. The component of the handpiece on which the thermocouple is provided and which comprises a material that is part of the thermocouple or of the thermocouple component is preferably formed by an outer shell of the handpiece or by a component of the handpiece, which is connected to the outer shell of the handpiece (in an electrically conducting manner), for example, a bearing for supporting a tool holder for the tool that can be connected to the handpiece or a contact ring.

According to a second embodiment, the electrical temperature-measuring device comprises a material whose electric resistance or dynamic resistance is variable as a function of the temperature. The material comprises, for example, an ohmic resistance, an electric conductor, in particular a metal, a ceramic (a sintered metal oxide) or a doped semiconductor. Preferably at least one of these materials is part of a sensor of the electrical temperature-measuring device. Depending on the embodiment, such a sensor is designed as an active sensor which needs a current or voltage supply for determining the temperature, or as a passive sensor which needs no voltage or current supply for determining the temperature.

According to an alternative embodiment, a medical or dental instrument, preferably a handpiece is provided, comprising a temperature-measuring device for measuring the temperature in an instrument or at least a part of the instrument, wherein the temperature-measuring device comprises a magnetic material, at least one magnetic property of the magnetic material, preferably the magnetic flux density or the magnetic susceptibility being dependent on the temperature and/or having a temperature-dependent characteristic. A corresponding method for measuring the temperature of at least a part of a medical or dental instrument, preferably handpiece or in or on a medical or dental instrument, preferably handpiece is defined in that at least one magnetic property of the magnetic material, preferably the magnetic flux density or the magnetic susceptibility is altered by a change in temperature.

According to another alternative embodiment, a medical or dental handpiece is provided, comprising a handle part, a coupling part for connecting the handpiece to at least one media source and/or an energy source, a head part having a holding device that can be set in motion for a tool, a temperature-measuring device for measuring the temperature in the handpiece or of at least a part of the handpiece, which is designed to provide an electrical temperature-measuring signal and an electrical switching device, which is electrically connected to the temperature-measuring device and to a signal device to receive the temperature-measuring signal supplied by the temperature-measuring device and to switch the signal device at least between a first signal condition and a second signal condition which is different from the first signal condition when the temperature-measuring signal reaches or exceeded or falls below a limit value.

Due to the use of a temperature-measuring device, which supplies an electric temperature measure signal, an electrical switching device and a signal device, which is provided on the handpiece and is preferably also operated electrically, a handpiece with a precise and rapid temperature measurement and temperature display which in particular displays the fact that a temperature limit value has been reached, exceeded or underrun is created in an advantageous manner.

The temperature-measuring device may comprise, for example, at least one thermocouple or a pyrometer or an infrared sensor or an optical conductor for electromagnetic radiation whose scattering or refractive index is a function of temperature or a temperature sensor whose electric or dynamic resistance is a function of temperature or additional temperature sensors, in particular all the temperature sensors mentioned below.

The electrical switching device preferably comprises a comparator circuit, which is designed to compare the measured temperature signal supplied by the temperature-measuring device with a predetermined limit value or reference value, in particular one that can be adjusted by a user. The switching device controls the signal device on the basis of this comparison, in particular by delivering a switch signal to activate or deactivate the signal device on reaching or exceeding or dropping below the limit value. The electrical switching device is designed in particular as a microcontroller or as a microcomputer.

According to one embodiment, the electrical switching device and/or the temperature-measuring device and/or the signal device can be connected to an energy source located outside of the handpiece by way of the coupling part for supplying electric energy, in particular they can be connected to an energy supply of a dental unit or a control and/or regulating unit.

Alternatively, the electrical switching device and/or the temperature-measuring device and/or the signal device is/are connected to an energy source provided in or on the handpiece for supplying electric energy. Thus in an advantageous manner this creates a handpiece, which is completely independent of other devices with respect to the temperature measurement, processing and display, and this handpiece can in particular be connected with no problem to existing power supply or control equipment. Such a completely independent handpiece is preferably created by providing an electrodynamic transducer (generator) on or in the handpiece, said transducer being operable by a driveshaft of the handpiece or by a fluid that can be conveyed in the handpiece.

Alternatively, an energy storage mechanism, in particular a battery or a rechargeable battery is provided as the energy source provided in or on the handpiece. Thus a temperature measurement which is independent of operation of the driveshaft or of the conveyance of the fluid may be provided in an advantageous manner.

The first signal condition and the second signal condition preferably comprise a visually perceivable and/or acoustically perceivable and/or tactilely perceivable signal which can be emitted directly to the user or in the direction of the user, in particular from the outer surface or outer shell of the handpiece and/or through the outside surface or outer shell. A particularly rapid transmission of information about the temperature of the handpiece, in particular about reaching, exceeding or falling below a temperature limit value, can thus be supplied to the user.

The signal device has a light source, for example, in particular an optical semiconductor element or an LCD display. The light source is preferably arranged in or on the outside surface or outer shell of the handpiece.

According to one embodiment, the signal device, in particular the light source, is designed to represent the first signal condition by displaying a first color and to represent the second signal condition by displaying a second color, which is different from the first color. Alternatively, the signal device, in particular the light source, is designed to represent the first signal condition by emitting light from the handpiece and to represent the second signal condition by not emitting light from the handpiece. In both embodiments it is thus possible to inform the user about the temperature of the handpiece, in particular when it reaches, exceeds or falls below a temperature limit value, rapidly and unambiguously.

The signal device preferably includes a lighting device, which is arranged on the handpiece such or is designed such, that it illuminates a tool that can be inserted into the holding device of the handpiece and/or illuminates the treatment site. This lighting device is in particular arranged on the head part of the handpiece or next to the head part of the handpiece or on a section of the handle part adjacent to the head part. Thus only one lighting device or light source is advantageously needed, this light device or light source being designed both for illuminating the tool and/or the treatment site and for providing information about the temperature of the handpiece or a part of the handpiece. It is thus advantageously not necessary for the user to turn away from the treatment site, in particular when doing a treatment if he wishes to obtain information about the temperature of the handpiece.

According to one embodiment, the signal device, in particular the light source, is provided on the handle part or on the coupling part of the handpiece, in particular on a side of the handle part or the coupling piece, which is pointing away from or opposite a tool receptacle opening of the handpiece, thus achieving a particularly good visibility of the signal device for the user.

To permit the most rapid and accurate possible temperature measurement, the temperature-measuring device is preferably arranged close to at least one heat source, preferably in or adjacent to the head part of the handpiece and/or on or near a moving component of the handpiece, for example, on a bearing, a shaft, a holding device for a tool that can be connected to the handpiece or a releasing device for a tool that can be connected to the handpiece. As the heat source whose temperature can be determined by means of the temperature-measuring device, however, a drive, for example, an electric motor that is provided in the handpiece or another device, which can be operated with electric energy, for example, may also be designed.

The temperature-measuring device is preferably designed to measure the temperature of the handpiece or of a part of the handpiece contact-freely by detection of electromagnetic radiation, in particular thermal radiation and/or the temperature-measuring device is designed to measure the temperature of an interior of the handpiece that can be heated by at least one heat source. The temperature measurement may thus advantageously be performed very rapidly and independently, in particular at a spatially separate location from the heat source, as also described below in detail.

The handpiece preferably has at least two parts that are detachably connected to one another, wherein the electrical switching device and/or the temperature-measuring device and/or the signal device and/or the energy source provided in or on the handpiece is/are arranged in different parts. The parts detachably connected to one another comprise, for example, the handle part and a head part that can be separated from the handle part or a handle part and a coupling part that can be separated from it for connecting the handpiece to at least one media source and/or one energy source.

The term "handpiece" comprises in particular medical or dental devices that can be held in the hand, for example, straight, pistol-shaped, angled or bent handles, which are often referred to in the dental field as contra-angle handpieces, parts of handpieces or handles, in particular a head section, which can be connected to a detachable handle section, for example, as well as couplings, adapters, connecting pieces and drive units, for example, electric or pneumatic motors. The term "handpiece" is also understood to refer to both cordless handpieces, in particular with a replaceable or rechargeable energy source, as well as handpieces that comprise a power supply line and a control, regulating and/or power supply unit connected to it. According to a preferred embodiment, which can be applied to all embodiments and examples herein, the handpiece comprises a handpiece head in which a tool holder for the tool that can be connected to the handpiece and the temperature-measuring device, in particular the temperature sensor of the temperature-measuring device are provided.

These and other embodiments will be described below with reference to the following drawings.

BRIEF DESCRIPTION OF THE DRAWINGS

FIGS. 17-23 show embodiments of medical or dental instruments, preferably handpieces or components of such instruments having a temperature-measuring device for measuring the temperature in the instrument or at least a part of the instrument, wherein the temperature-measuring device comprises a magnetic material, wherein at least one magnetic property of the magnetic material, preferably the magnetic flux density or the magnetic susceptibility is a function of temperature and/or has a temperature-dependent course.

DETAILED DESCRIPTION

Figure 1:
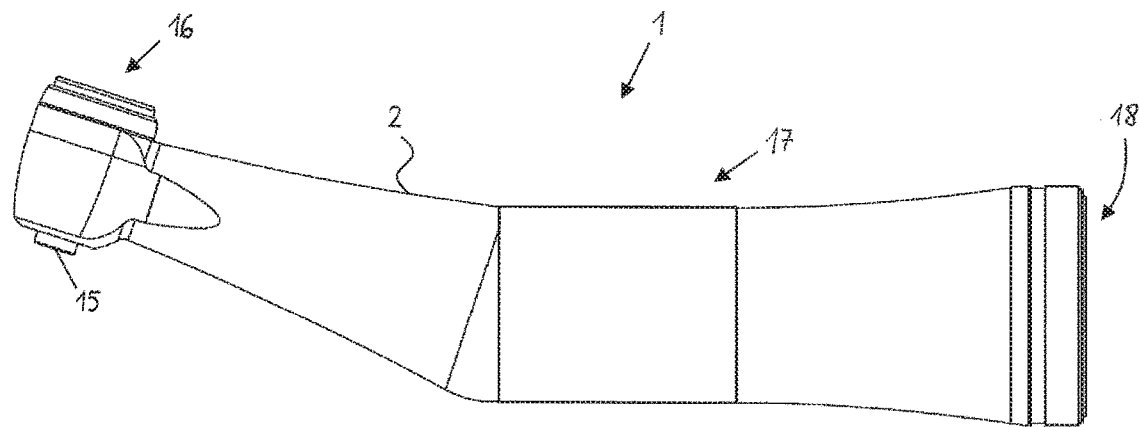
FIG. 1 shows an outside view of an embodiment of a handpiece, having a temperature-measuring device for measuring the temperature of the handpiece or of a part of the handpiece.

FIG. 1 shows an outside view of an angled handpiece 1, which is often referred to as a contra-angle handpiece, having an outer shell 2. The handpiece 1 has a handle part 17, one that is angled in particular, and a head part 16 in which a tool holder 15 is arranged for detachable connection or for holding a tool that can be connected to the handpiece 1. The tool holder 15 is preferably arranged movably in the handpiece 1, for example, rotatably, wherein the rotatability is ensured in particular by bearings 5, preferably roller bearings or ball bearing (see FIG. 2).

A coupling or connecting device 18, which is designed to connect the handpiece 1 to one or more fluid sources, for example, a liquid source, in particular water or a gas source, in particular compressed air is provided on the end of the handpiece 1 opposite the head part 16. The handpiece 1 can preferably also be connected to an electric voltage source and/or to a drive device, for example, an electric motor or a pneumatically operable motor by the connecting device 18. Optionally additional electric lines or contacts are provided for data and/or signal transmission to the coupling device 18.

One or more fluid lines extend through the handpiece 1 and/or the outer shell 2 from the connecting device 18 in the direction of the head part 16 or into the head part 16. The handpiece 1 optionally also has one or more shafts 19, preferably connected by gearwheels or gears 6, which serve as the drive device 3 and transmit a drive movement to the tool holder 15 (see FIG. 2).

Figure 2:
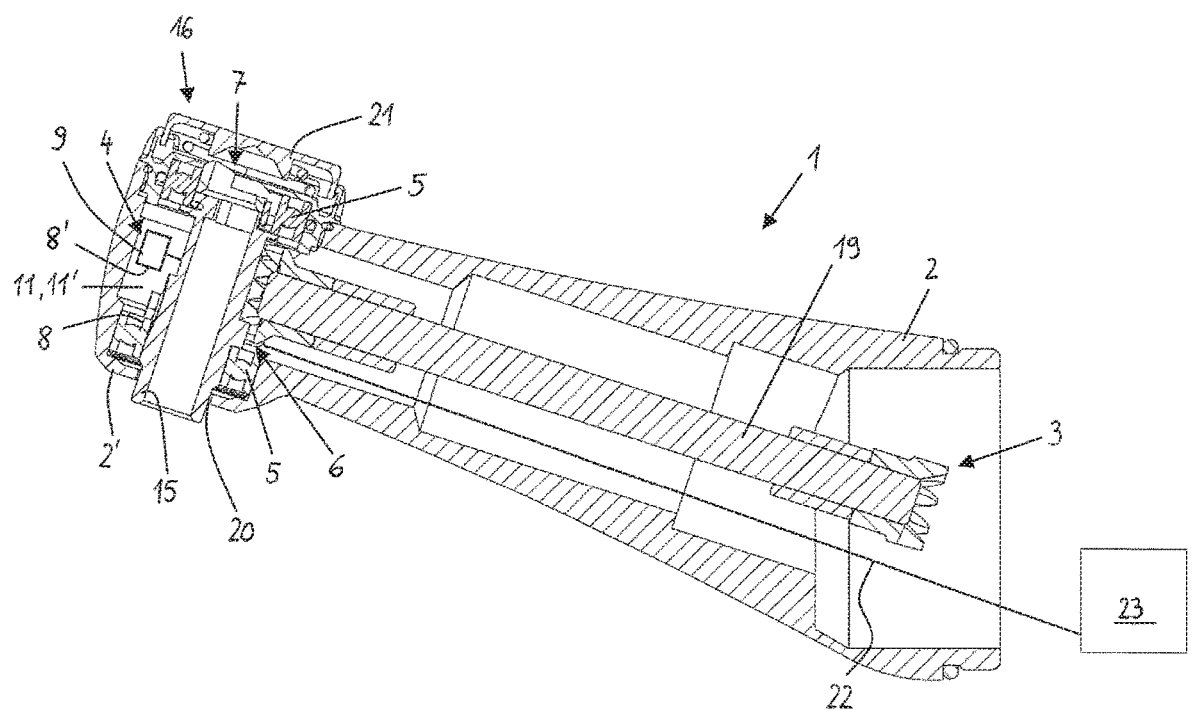
FIG. 2 shows an embodiment of a handpiece head having a temperature-measuring device for measuring the temperature of the handpiece or of a part of the handpiece, wherein the temperature-measuring device comprises a pyrometer or an infrared sensor.

FIG. 2 shows a section through a part of the handle part 17 and in particular through the head part 16 of the handpiece 1. The head part 16 has a hollow head shell T which forms an interior space 11. The interior space 11 is designed in particular as a volume 11' containing a fluid, in particular air, in which different components of the head part are accommodate, for example, components that are stationary with respect to the shell 2, 2' or components that are movable with respect to the shell 2, 2', in particular the bearing 5, the tool holder 15, at least parts of a gear 6 or of gearwheels, which transfer the driving movement of the drive device 3 from the shaft 19 to the tool holder 15, at least parts of a device 7 for releasing a tool from the tool holder or additional components such as spring elements, supporting elements, etc. In addition, on one side of the head part 16, an opening 20 through which the tool can be inserted into the head part 16 or into the tool holder 15 and/or can be removed from it is provided. On the side of the head part 16, which is opposite the opening 20, an actuating element 21 is provided for actuating the tool-releasing device 7, in particular a pressure element or a pressure cover.

At least some of the components or parts thereof mentioned above may be designed as heat sources, for example, the bearings 5, the gear 6 or the tool-releasing device 7. However, other components of the handpiece may of course also form heat sources, in particular a component that emits electromagnetic radiation, for example, an illuminating device, a heating element for media, an electrical or electronic component, etc. What all these heat sources have in common is that they release heat into the interior of the handpiece 1 and/or to the outer shell 2, 2' of the handpiece. To determine the temperature of the handpiece 1 or of a part of the handpiece 1, preferably of the outer shell 2, 2' or of the interior space 11 of the handpiece 1 and in particular to prevent excessive heating, a temperature-measuring device 4 is provided in or on the handpiece 1, in particular in or on the head part 16.

The temperature-measuring device 4 is connected by an electric line or a signal line 22 to a unit 23, which is optionally designed as an evaluation unit for evaluating the measured signals of the temperature-measuring device 4 and/or as a regulating or control unit for temperature-dependent regulation or control of the operation of the handpiece 1, for example, for interrupting the operation of the handpiece 1 on reaching or exceeding a predetermined temperature limit value and/or as a display unit for displaying the measured or determined temperature value or a temperature limit value. Preferably at least portions of the unit 23 are provided in or on the handpiece 1. According to a particularly preferred embodiment, the entire temperature-measuring device 4 including the line 22 and the unit 23 is arranged in or on the handpiece 1 thus resulting in particular in a handpiece 1, which is independent with respect to the temperature measurement, temperature analysis and the corresponding control or regulation.

The features described above with reference to FIGS. 1 and 2 apply to all the embodiments illustrated in FIGS. 2-13. The features in which the handpieces 1 of FIGS. 2-13 can be differentiated, preferably the different temperature-measuring devices 4, will be described now in particular.

Figure 3:
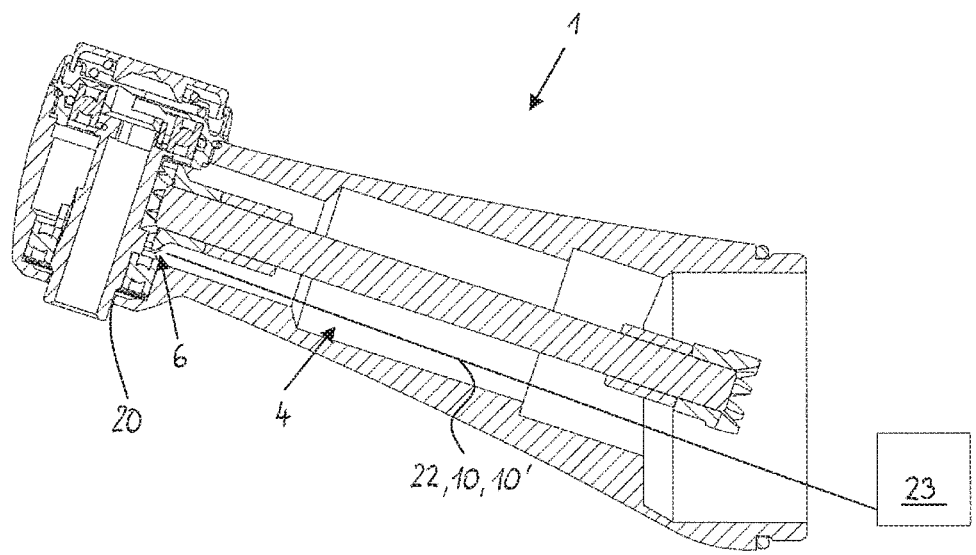
FIGS. 3 and 4 show two embodiments of handpiece heads, each having a temperature-measuring device for measuring the temperature of the handpiece or of a part of the handpiece, wherein the temperature-measuring devices each comprise an optical conductor for electromagnetic radiation, the scattering or refractive index of which varies as a function of changes in temperature.
Figure 4:
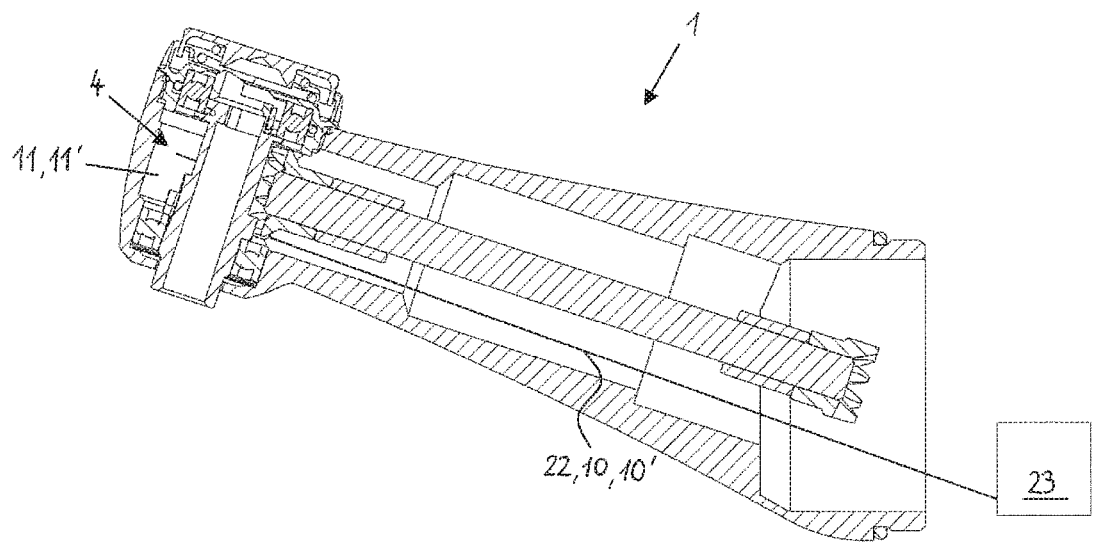

Each handpiece 1 of FIGS. 2-4 has a temperature-measuring device 4, which is designed to measure the temperature of the handpiece 1 or of a part of the handpiece 1 or of the interior space 11, which can be heated by the heat sources 5, 6, 7. This is done contact-freely by detection of electromagnetic radiation, in particular thermal radiation.

The temperature-measuring devices 4 are arranged and/or designed according to FIGS. 1-4 in the handpieces 1 in such a way that they receive electromagnetic radiation from several heat sources (for example, the bearings 5, the gear 6 and parts of the tool-releasing device 7) arranged in the outer shell 2 of the handpiece 1 in order to determine in particular an average temperature value of the several heat sources 5, 6, 7. To receive the thermal radiation of the several heat sources 5, 6, 7, at least one of the following features is implemented: the temperature-measuring device 4 is arranged in the interior space 11, 11' of the handpiece 1 at a distance from the heat sources 5, 6, 7; the temperature-measuring device 4 is arranged between the heat sources 5, 6, 7; the heat sources 5, 6, 7 surround the temperature-measuring device 4; the electromagnetic radiation-emitting surfaces 8 (only one such surface on a bearing 5 is shown as an example in FIG. 2) of the heat sources 5, 6, 7 are arranged at a distance from a surface 8' of the temperature-measuring device 4 receiving the electromagnetic radiation of the heat source 5, 6, 7; or the temperature-measuring device 4 comprises several surfaces 8' which receive the electromagnetic radiation of the heat sources 5, 6, 7 and which face in different directions in particular.

The temperature-measuring device 4, in particular the sensor of the temperature-measuring device 4, is preferably arranged between the two bearings 5 supporting the tool holder 15 and/or in the vicinity of the head shell 2', in particular on the inside of the jacket of the head shell 2' extending between the actuating element 21 and the tool opening 20 and/or in a space between the head shell 2' and the tool holder 15 and/or in a space bordered by the head shell 2, the tool holder 15 and the two bearings 5 (see FIGS. 2 and 4). Alternatively, the temperature-measuring device 4, in particular the sensor of the temperature-measuring device 4 is arranged in the area of tool-releasing device 7, in particular between the bearing 5, which is situated closer to the actuating element 21, and the actuating element 21. Alternatively, the temperature-measuring device 4, in particular the sensor of the temperature-measuring device 4, is arranged near the bearing 5, which is closer to the tool opening 20 and/or in the area of the gear 6 and/or between the aforementioned bearing 5 and the gear 6 (see FIG. 3).

The temperature-measuring device 4 according to FIG. 2 comprises in particular a pyrometer or an infrared sensor 9, which is designed in particular to detect electromagnetic radiation in a range from approximately 5 µm to approximately 20 µm. The pyrometer or the infrared sensor 9 is preferably designed as a semiconductor sensor. Preferably, the pyrometer or the infrared sensor 9 additionally comprises a device for self-temperature compensation, in particular a resistor.

The temperature-measuring devices 4 according to FIGS. 3 and 4 comprise an optical conductor 10 for electromagnetic radiation, in particular a fiber rod 10', preferably made of quartz glass, whose scattering or refractive index in particular in the temperature-sensitive section varies because of changes in temperature. An electromagnetic radiation source which emits radiation into the optical conductor is provided in the unit 23. This radiation is directed through the optical conductor, is scattered or refracted as a function of the temperature of the handpiece 1 or of the interior space 11 and thus as a function of the scattering or the refractive index of the optical conductor 10 and then returns back to the unit 23. On the basis of the changes in the received radiation with respect to the radiation emitted by the radiation source, the unit 23 determines the temperature (fiber-optic temperature measurement or distributed temperature sensing).

As already described above, the end of the optical conductor 10 or the temperature-sensitive section of the optical conductor 10 is arranged either in the area of the bearing 5 situated closer to the tool opening 20 (see FIG. 3) or in a space between the head shell 2' and the tool holder 15 (see FIG. 4).

FIGS. 5-10 show different embodiments of a handpiece 1 with an electrical temperature-measuring device 12, which has at least one thermocouple 13 or a part thereof, i.e., a thermocouple component 13', in particular which is designed to provide an electric thermoelectric voltage signal for measuring the temperature. The thermocouple 13 comprises two different materials, in particular two different metals which are joined to one another at a point or in a section, in particular being joined by welding. An electric line 22 conducts the thermoelectric voltage signal or the measured signal of the thermocouple 13 to the unit 23, which determines the temperature value on the basis of the received signal.

Figure 5:
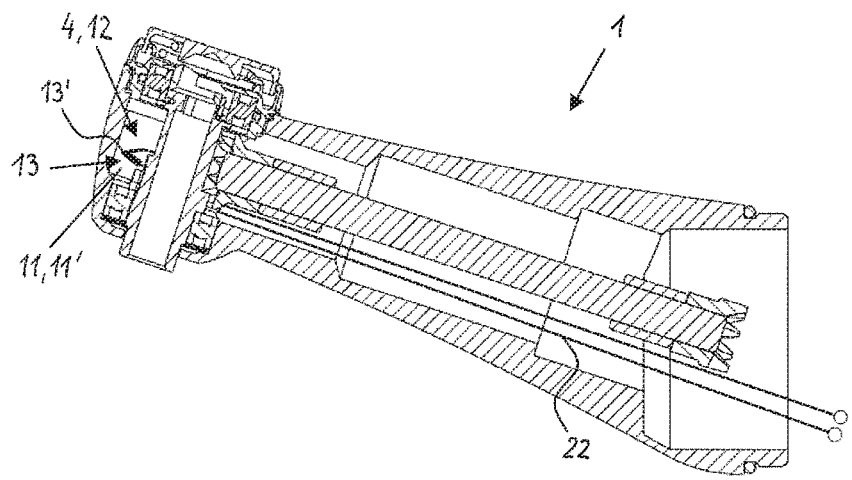
FIGS. 5-9 show embodiments of handpiece heads, each having a temperature-measuring device for measuring the temperature of the handpiece or of a part of the handpiece, wherein each temperature-measuring device comprises a thermocouple.

The thermocouple 13 or the thermocouple component 13' of FIG. 5 is designed and/or arranged to measure the temperature of the interior space 11 of the handpiece 1 that can be heated by the at least one heat source 5, 6, 7, preferably the temperature of the fluid contained in the interior space 11 or volume 11'. Alternatively, the thermocouple 13 or the thermocouple component 13' of FIG. 5 is designed and/or arranged in such a way that it determines an average temperature value by measuring the temperature of the interior 11, 11', in particular an average temperature value of multiple components and/or heat sources 5, 6, 7 of the handpiece 1, which deliver heat into the interior 11, 11' or to the fluid contained therein.

To be able to determine the temperature of the interior 11, 11', at least one of the following features is implemented: the thermocouple 13 or the thermocouple component 13' is arranged in the interior 11, 11' of the handpiece 1 at a distance from the heat sources 5, 6, 7; the thermocouple 13 or the thermocouple component 13' is arranged between the heat sources 5, 6, 7; the heat sources 5, 6, 7 surround the thermocouple 13 or the thermocouple component 13'; the heat-emitting surfaces 8 of the heat sources 5, 6, 7 are spaced a distance apart from the thermocouple 13 or the thermocouple component 13'.

FIG. 5 shows specifically a thermocouple 13, which is arranged between the two bearings 5 supporting the tool holder 15 and/or is arranged in the vicinity of the head shell 2', in particular on the inside of the jacket of the head shell 2' extending between the actuating element 21 and the tool opening 20 and/or is arranged in a space between the head shell 2' and the tool holder 15 and/or in a space bordered by the head shell 2, the tool holder 15 and the two bearings 5.

Figure 6:
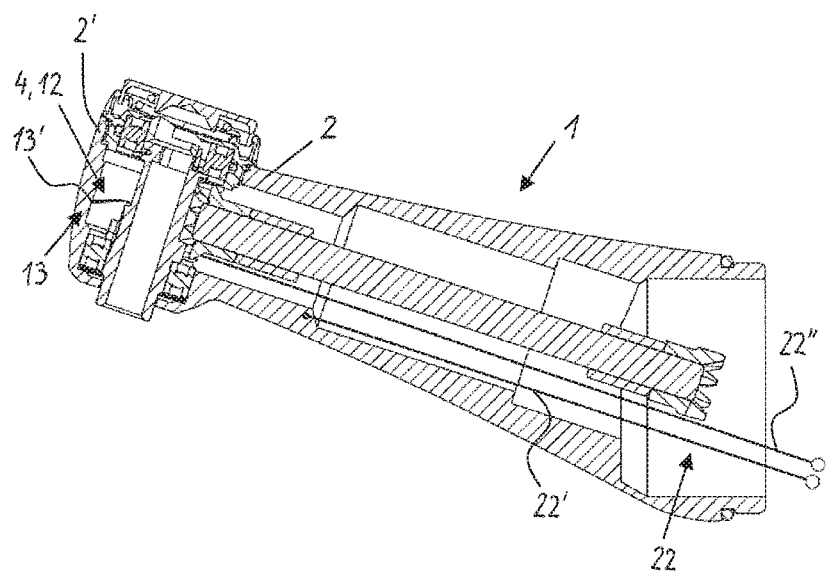
Figure 7:
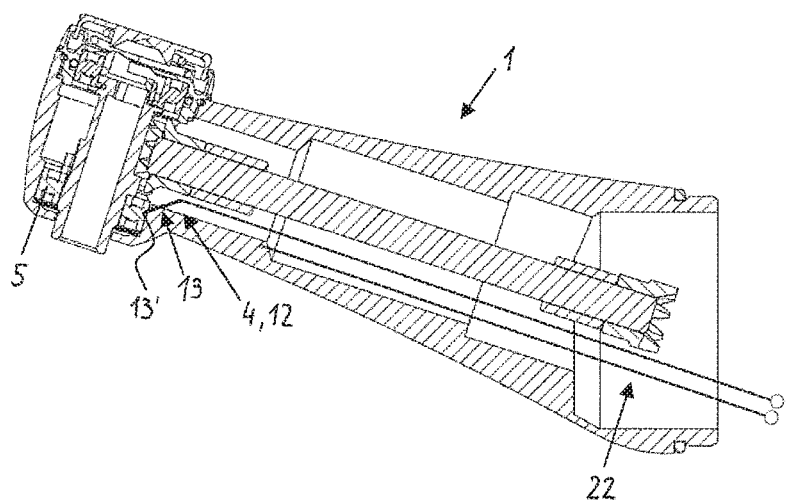

Alternatively, FIGS. 6 and 7 show two embodiments, in which the thermocouple 13 or the thermocouple component 13' is each provided on a component of the handpiece 1, namely the outer shell 2 (see FIG. 5) or a bearing 5 (see FIG. 6) so that the thermocouple 13 or the thermocouple component 13' preferably determines the temperature of this component. The component 2, 5 on which the thermocouple 13 or the thermocouple component 13' is provided is preferably made of a material, which is part of the thermocouple 13 or of the thermocouple component 13'.

One advantage of the embodiments depicted in FIGS. 6 and 7 is in particular that at least one electric conductor 22' of the electric line 22, which conducts the thermoelectric voltage signal to the unit 23, need collect the thermoelectric voltage signal directly on the thermocouple 13 or the thermocouple component 13' because of the use of a material of the outer shell 2, 2' as part of the thermocouple 13 or as the thermocouple component 13' or because of the electric connection of the outer shell 2, 2' to the thermocouple 13 or the thermocouple component 13' or because of the electric connection of the outer shell 2, 2' to the component 2, 5 whose material is part of the thermocouple 13 or of the thermocouple component 13', but instead the thermoelectric voltage signal can be collected at (any location on) the outer shell 2, 2'.

In other words the temperature device 4 according to FIGS. 6 and 7 comprises a thermocouple 13 or a thermocouple component 13' and an electric line 22 having two electric conductors 22', 22" for conducting the thermoelectric voltage signal generated by the thermocouple 13 or the thermocouple component 13' to the evaluation unit 23, wherein the thermocouple 13 or the thermocouple component 13' is provided on the outer shell 2, 2' or on a component connected (electrically) to the outer shell 2, 2', for example, the bearings 5 (to determine the temperature of the outer shell 2, 2' or of the component connected thereto), wherein the outer shell 2, 2' or the component comprises a material which is part of the thermocouple 13 or of the thermocouple component 13' and wherein one of the two conductors 22', 22" contacts (electrically) the outer shell 2, 2' of the handpiece 1, in particular contacting any location on the outer shell 2, 2', preferably a location on the outer shell 2, 2' at a distance from the thermocouple 13 or the thermocouple component 13', for example, the handle section 17 of the outer shell 2 or a section of the outer shell 2 connected to the head part 16 or the coupling or connecting device 18 or a location on the outer shell 2 situated between the thermocouple 13 or the thermocouple component 13' and the couplings or connecting device 18.

Alternatively, it is of course possible accordingly that one of the two conductors 22', 22" contacts (electrically) the component whose material is part of the thermocouple 13 or the thermocouple component 13', for example, the bearing 5, in particular contacting any location on the component. In this case, obviously an electric connection of the component to the outer shell 2, 2' is not necessary.

Figure 8:
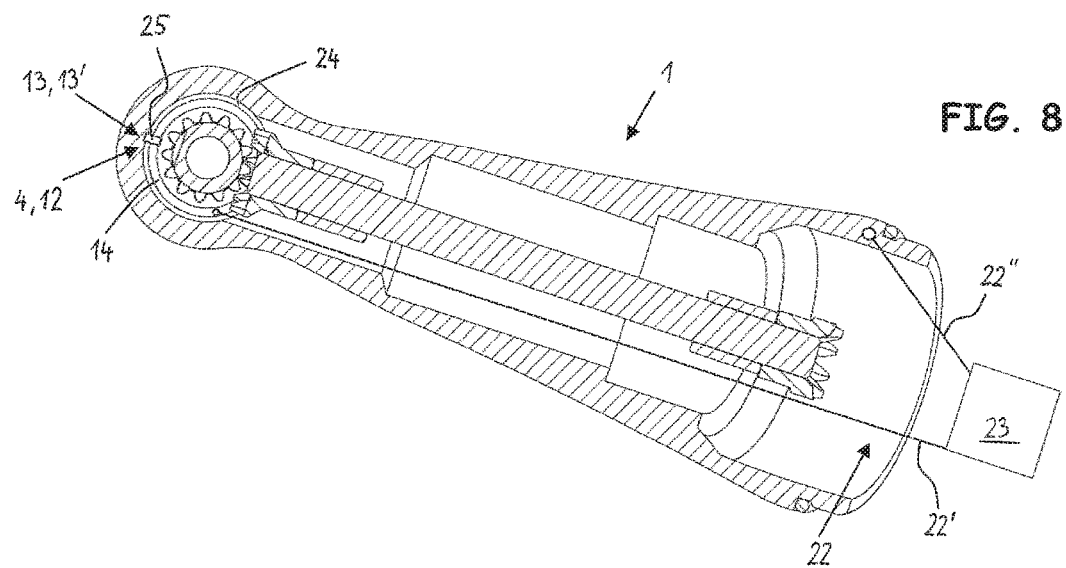
Figure 9:
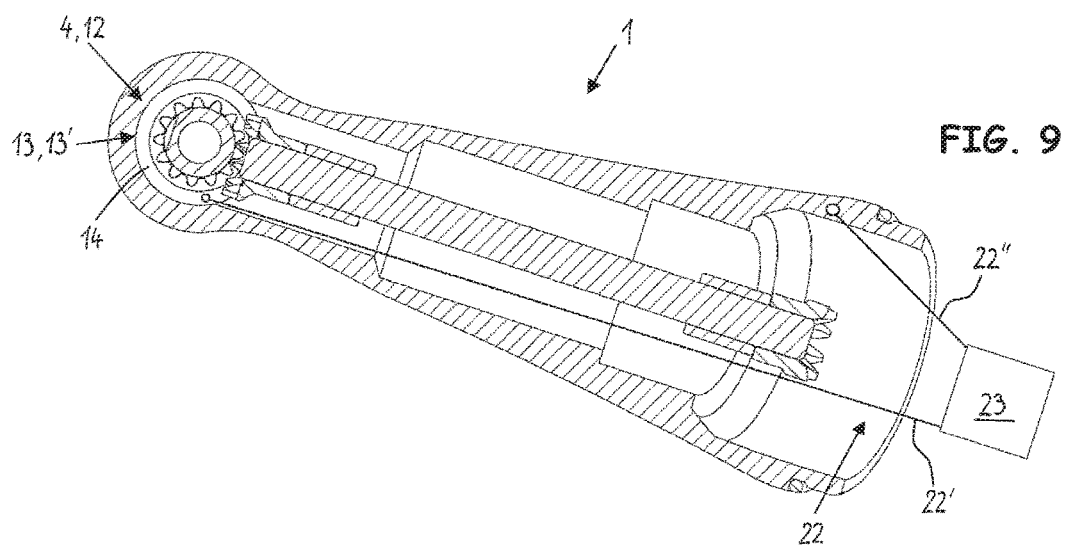

FIGS. 8 and 9 show two other embodiments of a handpiece 1 with a thermocouple 13 or a thermocouple component 13', wherein a contact ring 14, in particular a metallic contact ring, is provided in both embodiments and is part of the thermocouple 13 or forms the thermocouple component 13'.

The contact ring 14 in FIG. 8 is separated from the handpiece by electric insulation 24, for example, a ring-shaped insulation. The electric insulation 24 is provided in particular between the outer shell 2, 2' of the handpiece 1 and the contact ring 14. The insulation 24 is interrupted or has a passage at a contact location (spatially limited, narrow or point-shaped) or a contact point 25, so that direct electric contact is established between the contact ring 14, comprising a first material, and the outer shell 2, 2' of the handpiece 1, comprising a second different material. This contact point 25, which passes through the electric insulation 24 or the two materials of the outer shell 2, 2' and the contact ring 14 thus form the thermocouple 13 or the thermocouple component 13' for measuring the temperature. The thermoelectric voltage signal provided by the thermocouple 13 or the thermocouple component 13' thus represents a temperature value at the point of contact between the outer shell 2, 2' and the contact ring 14. The contact ring 14 is preferably provided in the area of the actuating element 21 for actuating the tool release device 7, in particular between the actuating element 21 and the bearing 5, which is closer to the actuating element 21.

The handpiece 1 in FIG. 9 has essentially the same design as the handpiece 1 in FIG. 8, but no electric insulation 24 is provided between the outer shell 2, 2' and the contact ring 14 so that instead of the point contact in FIG. 8, there is an electric surface contact here between the outer shell 2, 2' and the contact ring 14, i.e., their different materials, forming the thermocouple component 13'. The surface contact comprises for example, an angle of at least 5° of the circumferential surface of the contact ring 14, preferably at least 90°, in particular more than 180°. The thermoelectric voltage provided by the thermocouple 13 or the thermocouple component 13' thus represents an average temperature value at or over the surface contact between the outer shell 2, 2' and the contact ring 14.

An electric line 22 to conduct the thermoelectric voltage signal is also provided in each of the handpieces 1 in FIGS. 8 and 9, wherein one of the two conductors 22' contacts the contact ring 14 and the other of the two conductors 22" contacts the outer shell 2, 2'. As explained with reference to FIGS. 6 and 7, the conductor 22" may in turn contact the outer shell 22' at any location, preferably a location on the outer shell 2, 2' at a distance from the thermocouple 13 or the thermocouple component 13' or the contact ring 14, for example, the handle part 17 of the outer shell 2 or a section of the outer shell 2 connected to the head part 16 or the coupling or connecting device 18 or a location on the outer shell 2 arranged between the thermocouple 13 or the thermocouple component 13' and the coupling or connecting device 18.

Figure 10:
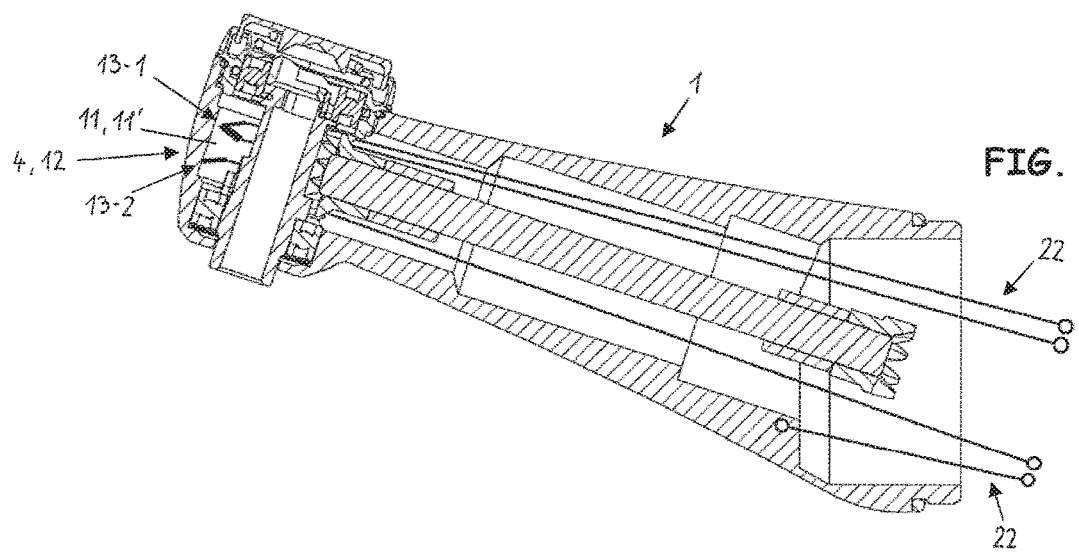
FIG. 10 shows an embodiment of a handpiece head having a temperature-measuring device for measuring the temperature of the handpiece or of a part of a handpiece, wherein the temperature-measuring device comprises two thermocouples.

It is of course also possible to provide multiple thermocouples 13 or thermocouple components 13' in one handpiece 1 as illustrated, for example, in FIG. 10. The handpiece 1 in FIG. 10 has a first thermocouple 13-1, which is provided freely, i.e., without direct contact with a component of the handpiece 1 in the interior 11, 11' to measure in particular the temperature of the fluid contained in the interior 11, 11', as described above for the handpiece 1 of FIG. 5. Accordingly all the features described in conjunction with the handpiece 1 or the thermocouple 13 in FIG. 5 can be applied or transferred to the handpiece 1 in FIG. 10 or to the thermocouple 13-1.

The handpiece 1 in FIG. 10 additionally has a second thermocouple 13-2, which is provided on a component of the handpiece 1. The component in particular comprises a material which is part of the thermocouple 13-2. The component is preferably formed by the outer shell 2, 2' as described above for the handpiece 1 of FIG. 6. Accordingly all the features described in conjunction with the handpiece 1 or the thermocouple 13 of FIG. 6 can be applied or transferred to the handpiece 1 of FIG. 10 or the thermocouple 13-2.

An electric line 22 leads from each thermocouple 13-1, 13-2 of the handpiece 1 to the unit 23, which receives the thermoelectric voltage signals of each thermocouple 13-1, 13-2 and processes them.

If a handpiece 1 has multiple thermocouples 13 or thermocouple components 13', then of course their numbers as well as their positions in the handpiece 1 or their design are freely selectable depending on the requirements or the intention regarding where the temperature is to be measured. Thus, for example, multiple free thermocouples 13-1 can be provided in a handpiece 1 without direct contact with a component of the handpiece and/or multiple thermocouples 13-2 may be arranged on one component and/or on multiple different components of the handpiece 1.

Figure 11:
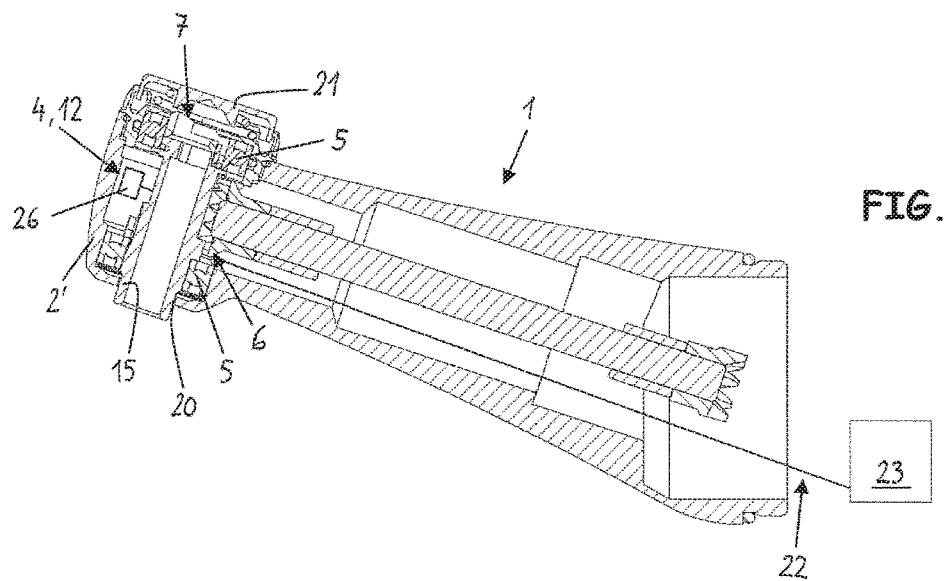
FIGS. 11-13 show embodiments of handpiece heads, each having one temperature-measuring device for measuring the temperature of the handpiece or of a part of the handpiece, wherein the electrical temperature-measuring device comprises a material whose electric resistance or dynamic resistance is variable as a function of the temperature.
Figure 12:
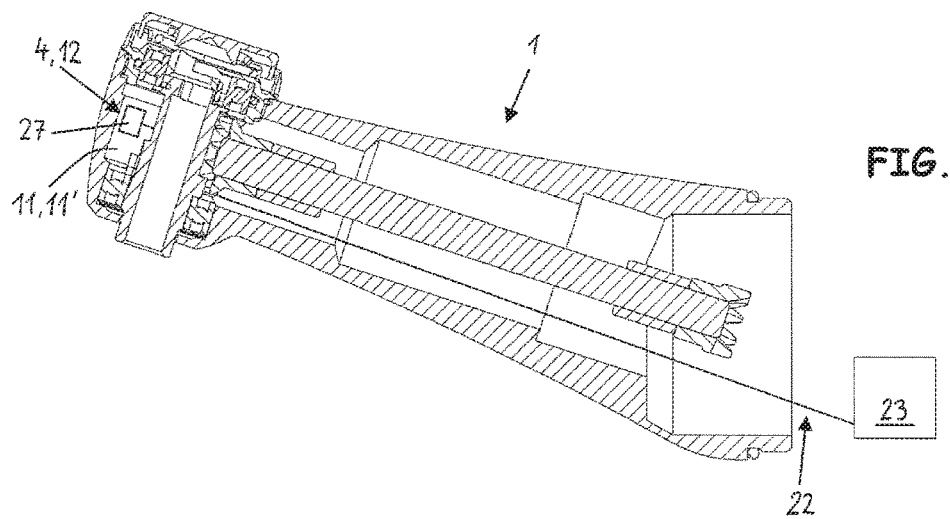
Figure 13:
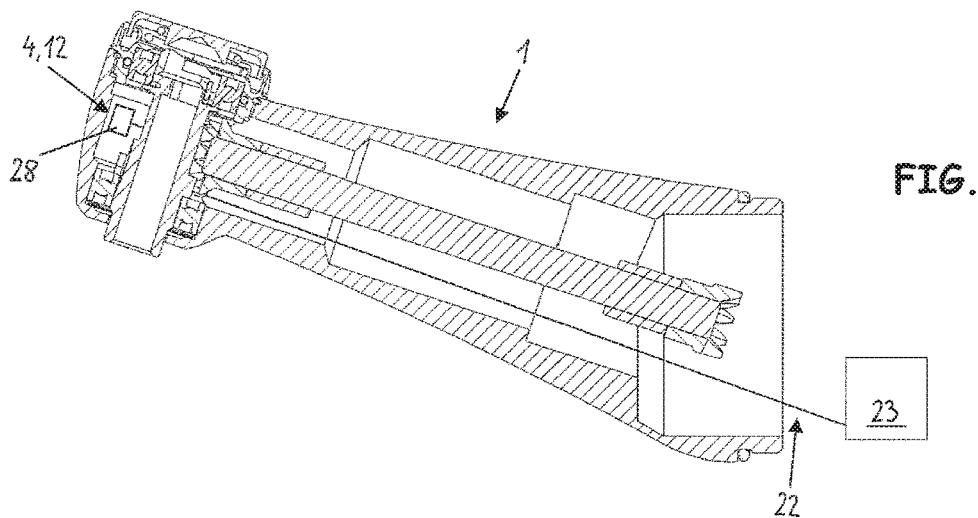

FIGS. 11-13 show handpieces 1 having additional electrical temperature-measuring devices 12, wherein each of these temperature-measuring devices 12 comprises a material whose electric resistance or dynamic resistance is variable as a function of temperature.

The temperature-measuring devices 4, 12 of FIGS. 11-13 are preferably arranged and/or designed in the handpieces 1 in such a way that they receive heat or thermal radiation from several heat sources arranged in the outer shell 2 of the handpiece 1 (for example, from the bearing 5, the gear 6 and parts of the workpiece-releasing device 7) to determine in particular an average temperature value of the several heat sources 5, 6, 7. To receive the heat or thermal radiation of the several heat sources 5, 6, 7, at least one of the following features is implemented: the temperature-measuring device 4, 12 is arranged in the interior 11, 11' of the handpiece 1 at a distance from the heat sources 5, 6, 7; the temperature-measuring device 4, 12 is arranged between the heat sources 5, 6, 7; the heat sources 5, 6, 7 surround the temperature-measuring device 4, 12; the heat-emitting surfaces of the heat sources 5, 6, 7 are placed at a distance from a surface of the temperature-measuring device 4, 12 receiving the heat of the heat source 5, 6, 7; the temperature-measuring device 4, 12 has multiple surfaces 8' receiving the heat of the heat source 5, 6, 7, these surfaces 8' pointing in different directions in particular.

Alternatively, the temperature-measuring devices 4, 12 of FIGS. 11-13 are designed and/or arranged to measure the temperature of the interior space 11 of the handpiece 1, which can be heated by the at least one heat source 5, 6, 7, preferably to measure the temperature of the fluid contained in the interior space 11 or the volume 11'.

The temperature-measuring device 4, 12, in particular the sensor of the temperature-measuring device 4, 12, is preferably arranged between the two bearings 5 supporting the workpiece holder 15 and/or in the vicinity of the head shell 2', in particular on the inside of the jacket of the head shell 2' extending between the actuating element 21 and the tool opening 20 and/or arranged in a space between the head shell 2' and the tool holder 15 and/or in a space bordered by the head shell 2, the tool holder 15 and the two bearings 5 (see FIGS. 2 and 4). Alternatively, the temperature-measuring device 4, 12, in particular the sensor of the temperature-measuring device 4, 12 is arranged in the area of the tool-releasing device 7, in particular between the actuating element 21 and the bearing 5 situated more closely to the actuating element 21. Alternatively, the temperature-measuring device 4, 12, in particular the sensor of the temperature-measuring device 4, 12 is arranged in the vicinity of the bearing 5 that is closer to the tool opening 20.

The temperature-measuring device 4, 12 of the handpiece 1 in FIG. 11 has a measuring resistor 26, which is preferably made of a noble metal whose electric resistance (ohmic resistance) is variable as a function of the temperature, in particular the temperature of the fluid in the interior 11, 11' surrounding the resistor 26. A current or voltage source provided in the unit 23 forms an electric circuit together with the electric line 22 and the measuring resistor 26. The change in the electric measured signal sent from the current or voltage source over the measuring resistor 26, in particular the voltage drop of a constant measuring current serving as a measuring signal is detected by a circuit of the unit 23 and used to determine the temperature. Additional elements for processing the measured signal are preferably present in the unit, for example, analog-digital converters, signal amplifiers or filters.

The temperature-measuring device 4, 12 of the handpiece 1 of FIG. 12 comprises a semiconductor sensor 27, preferably a semiconductor diode, in particular a doped silicon diode whose dynamic resistance (gate voltage at a p-n junction or at a metal-semiconductor junction of the semiconductor sensor 27) is variable as a function of the temperature, in particular the temperature of the fluid of the interior 11, 11' surrounding the semiconductor sensor 27. A current or voltage source provided in the unit 23 together with the electric line 22 and the semiconductor sensor 27 forms an electric circuit. The change in the electric measuring signal emitted by the current or voltage source and conducted over the semiconductor sensor 27, in particular the voltage drop of a constant measuring current serving as the measuring signal is detected by a circuit of the unit 23 and used to determine the temperature. Additional elements for processing the measuring signal, for example, analog digital converters, signal amplifiers or filters are preferably present in the unit.

The temperature-measuring device 4, 12 of the handpiece 1 in FIG. 12 has a metal resistor 28, wherein the voltage of the thermal resistance noise (i.e., the density fluctuations of the transport electrons of the resistor 28 due to their thermal motion) is variable as a function of the temperature, in particular the temperature of the fluid in the interior 11, 11' surrounding the resistor 28. A current or voltage source provided in the unit 23 forms an electric circuit together with the electric line 22 and the resistor 28. The change in the electric measuring signal emitted by the current or voltage source and conducted over the resistor 28, in particular the change in the electric voltage, is detected by a circuit of the unit 23 and used for determining the temperature. Additional elements for processing the measured signal, for example, analog-digital converters, signal amplifiers or filters are preferably present in the unit.

Figure 14:
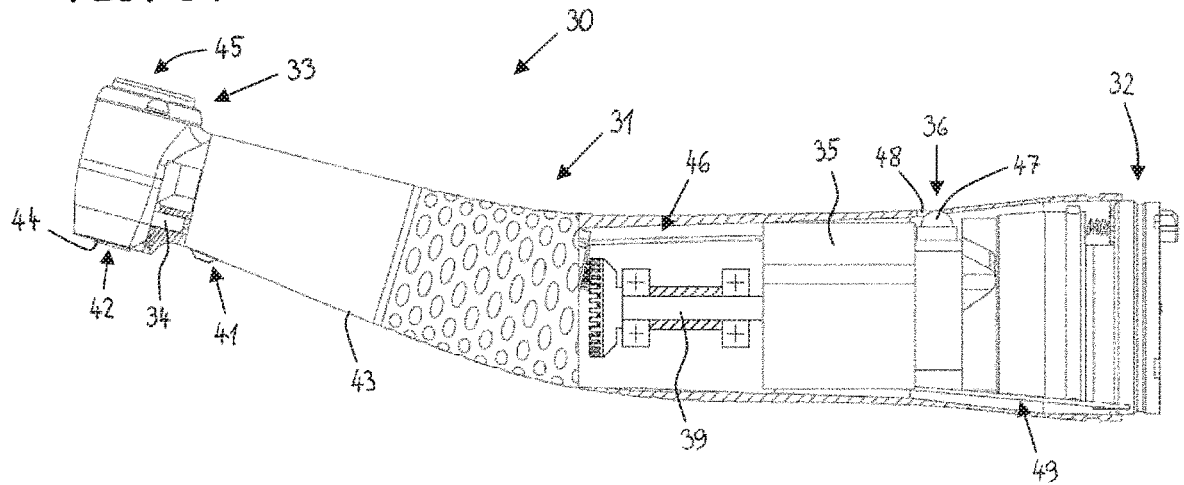
FIGS. 14-16 show embodiments of medical or dental handpieces, each having an electrical switching device, which is electrically connected to the temperature-measuring device and to a signal device.
Figure 15:
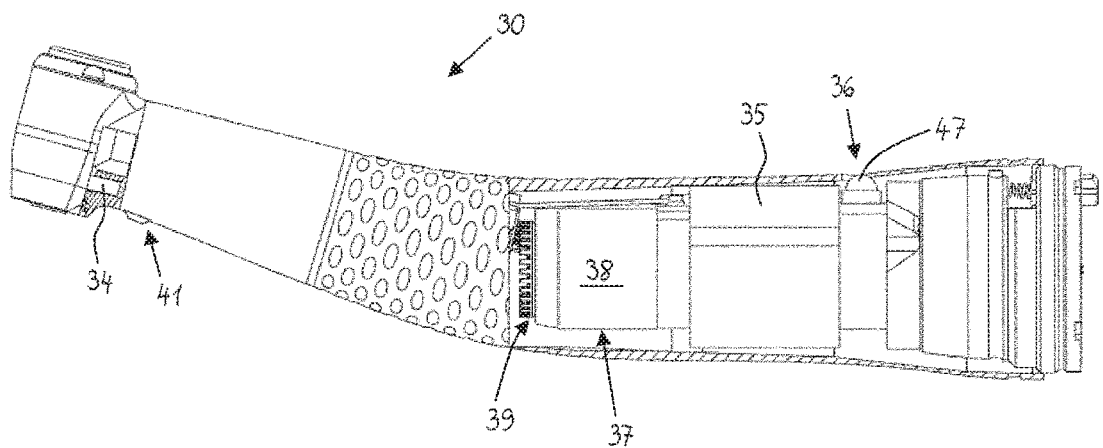
Figure 16:
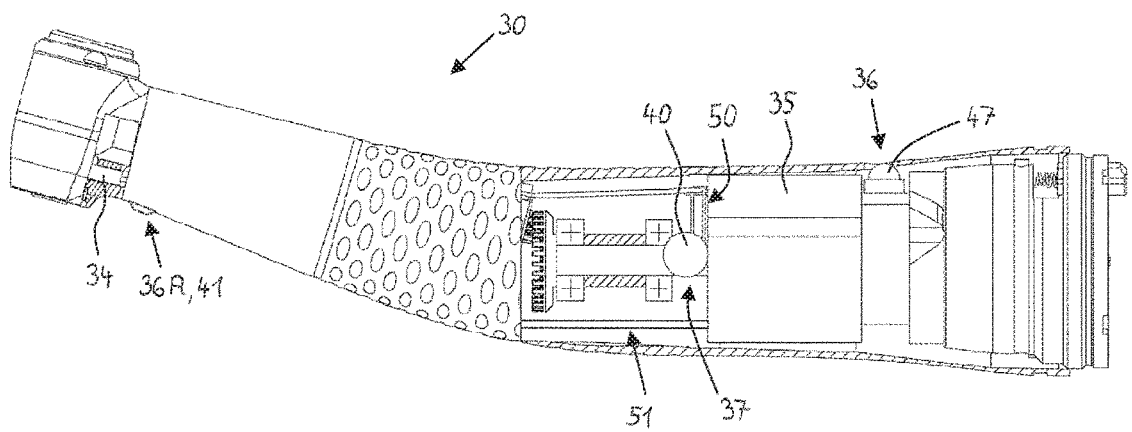

FIGS. 14-16 shows handpieces or contra-angel handpieces 30 with a temperature measurement which is largely or completely independent of a control, regulating and/or power supply unit. First the features and components shared by the handpieces 30 in FIGS. 14-16 will be described:

The handpiece 30 or its outer shell 43 comprises a handle 31 for holding the handpiece 30, in particular during operation of the handpiece 30, a coupling part 32 connected or connectable thereto for connecting the handpiece 30 to at least one media source and/or an energy source, in particular for connection to a control, regulating and/or power supply unit, and a head part 33 that is connected or connectable to the handle part 31 and has a holding device 42 for a tool and can be set in motion. The holding device 42 comprises, for example, a force-locking wrench or a positive holding device for the tool. The tool can be introduced into the holding device 42 or released from it through a tool receptacle opening 44 provided in the head part 33 or in its outer shell. In addition, a releasing device 45 with which the tool can be released from the holding device 42 is provided on the head part 33.

A lighting device 41, which emits light in the direction of the tool and/or the treatment site is provided on or arranged adjacently to the head part 33. The lighting device 41 comprises, for example, an optical semiconductor element, which emits light or an incandescent bulb and/or an optical waveguide, for example, one or more optical fibers or a glass rod.

The handpieces 30 shown in FIGS. 14-16 can be operated mechanically, preferably by motor, in particular by means of an electric motor and have at least one drive shaft 39, preferably having a gearwheel which is designed for transmitting a driving movement to the holding device 42. However, it is of course equally possible to drive and set in motion the holding device 42 by means of a drive fluid, in particular compressed air, in particular with a rotor which is connected to the holding device 42 and can be acted upon by the drive fluid.

It can be seen from the preceding that at least one movable component is arranged in the handpiece 30, for example, the driveshaft 39, the holding device 42, the rotor or the bearings, preferably roller bearings or ball bearings which support in particular the aforementioned components in the handpiece 30. Substantial heating of the handpiece 30 or parts thereof may occur due to the movement of this at least one movably arranged component and/or of a relative movement and thus friction between this at least one movable component and the outer shell 43 or a component held in the outer shell 43 in a rotationally fixed manner. Another heat source may of course also cause the heating of the handpiece 30, for example, a device that can be operated with electric energy, preferably a motor, a heating device or a lighting device.

To be able to measure and/or display and/or monitor and/or influence the temperature of the handpiece, a temperature-measuring device 34 is provided on the handpiece 30. The temperature-measuring device 34, in particular at least one temperature sensor of the temperature-measuring device 34 may be provided at any location or on any part 31, 32, 33 of the handpiece 30, preferably near at least one heat source or at a location on the handpiece 30, which often comes in contact with the user or a patient, in particular in the head part 33 or adjacent to the head part 33 in which components that are movable and/or movable in relation to one another are often arranged or on at least a part of the releasing device 45, in particular on or near its pushbutton or actuating element. The temperature-measuring device 34 or its temperature sensor may comprise, for example, a thermocouple or an infrared sensor.

The temperature-measuring device 34 is designed to supply an electrical temperature-measuring signal which can be transmitted to an electrical switching device 35. The transmission of the temperature-measuring signal preferably takes place in a hardwired operation by means of an electric line 46, which connects the temperature-measuring device 34 to the switching device 35. The switching device 35, in particular in the form of a microcontroller is designed to compare the electrical temperature-measuring signal with a reference value, in particular with a temperature limit value and to switch a signal device 36 at least between a first signal condition and a second signal condition which differs from the first signal condition when the temperature-measuring signal reaches, exceeds or falls below the reference value or the temperature limit value. The first and second signal conditions and/or the change between the two signal conditions are designed so that they draw the attention of the user to the fact that the temperature limit value has been reached, exceeded or not met.

The signal device 36, which is preferably in turn connected by means of electric lines to the switching device 35 comprises according to FIGS. 14-16 a light source 47, in particular at least one LED. However, alternatively or additionally, the signal device 36 may also have another signal generator, for example, an element that can be induced to oscillation that is acoustically and/or tactilely perceptible by the user. The signal device 36 is arranged on the coupling part 32 or on the handle part 31 close to the coupling part 32 according to FIGS. 14-16, but it may also be provided on any other location on the handpiece 30, in particular on a side of the handpiece 30 facing away from the tool receptacle opening 44, which faces the user during the treatment or is readily visible for the user. Preferably an opening 48 through which the signal device 36 can emit its signal, in particular the light source 47 can emit its light is preferably provided in the outer shell 43. Preferably at least a portion of the signal device 36, in particular of the light source 47 is arranged in this opening 48.

The electric power supply to the temperature-measuring device 34, the switching device 35 and optionally also the signal device 36 is different in the handpieces 30 according to FIGS. 14-16:

The handpiece 30 of FIG. 14 can be connected via the coupling part 32 to an energy source situated outside of the handpiece 30, wherein electric contacts that are detachably connectable to the energy source are provided on the coupling part 32. An electric line 49 arranged in the handpiece 30 connects the electric contacts on the coupling part 32 to the power-consuming devices 34, 35, 36 mentioned above. The electric line 49 preferably connects the contacts directly to the switching device 35, which is provided in particular with a device for adjusting the current or the voltage in order to supply the required voltage and/or the required electric current to the other power-consuming devices 34, 36. In particular, the switching device 35 is designed to use at least some of the electric energy as a switch signal for the signal device 36 (the latter also applies to the handpieces shown in FIGS. 15 and 16).

FIGS. 15 and 16 show two embodiments of handpieces 30 in which the electric power is supplied by an energy source 37 provided in or on the handpiece 30. According to FIG. 15 the handpiece 30 has an electrodynamic converter (generator) 38, which can be operated by the driveshaft 39 and generates electric energy as soon as the shaft 39, which is connected to a rotor of the generator 38, is set in rotation. The design of such a generator 38 is known from the prior art, so that it need not be discussed further here. An electric line is provided for transmission of the electric energy generated by the generator 38 to the power-consuming devices 34, 35, 36.

Alternatively FIG. 16 shows a handpiece 30, whose power source 37 provided in or on the handpiece 30, is formed by an energy-storing mechanism 40, in particular by a battery or a repeatedly rechargeable battery. An electric line 50 is provided for transmission of the electric energy from the energy storage mechanism 40 to the power-consuming devices 34, 35, 36.

FIG. 16 additionally shows another electric line 51, which supplies electric energy to the lighting device 41, comprising, for example, an optical light-emitting semiconductor element or an incandescent bulb. The lighting device 41 is designed to emit light in the direction of the tool and/or the treatment site. In addition, the lighting device 41 is designed as a signal device 36A, which can be switched by the switching device 35 at least between a first signal condition and a second signal condition that differs from the first signal condition when the temperature-measuring signal reaches, exceeds or falls below a limit value. Preferably, the first signal condition is defined by the emission of light by the lighting device 41 and the second signal condition is defined by no emission of light.

The electric line 51 connects the switching device 35 to the lighting device 41 and thus permits the switching device 35 to switch the lighting device 41 between the two signal conditions, for example, by interrupting and closing the electric power supply to the lighting device 41. The lighting device 41 can be supplied either with electric energy from an energy source situated outside of the handpiece 30 or from an energy source 37 situated in or on the handpiece 30.

When the lighting device 41 is designed as a signal device 36A, it is preferably also possible to omit the signal device 36 so that the lighting device 41 is the only signal device switchable by the switching device 35 for the temperature display. In addition, the lighting device 41 designed as a signal device 36A is clearly not limited to the embodiment in FIG. 16, but instead can be implemented accordingly in the handpieces 30 of FIGS. 14, 15, preferably again with the omission of the respective signal devices 36.

Figure 18:
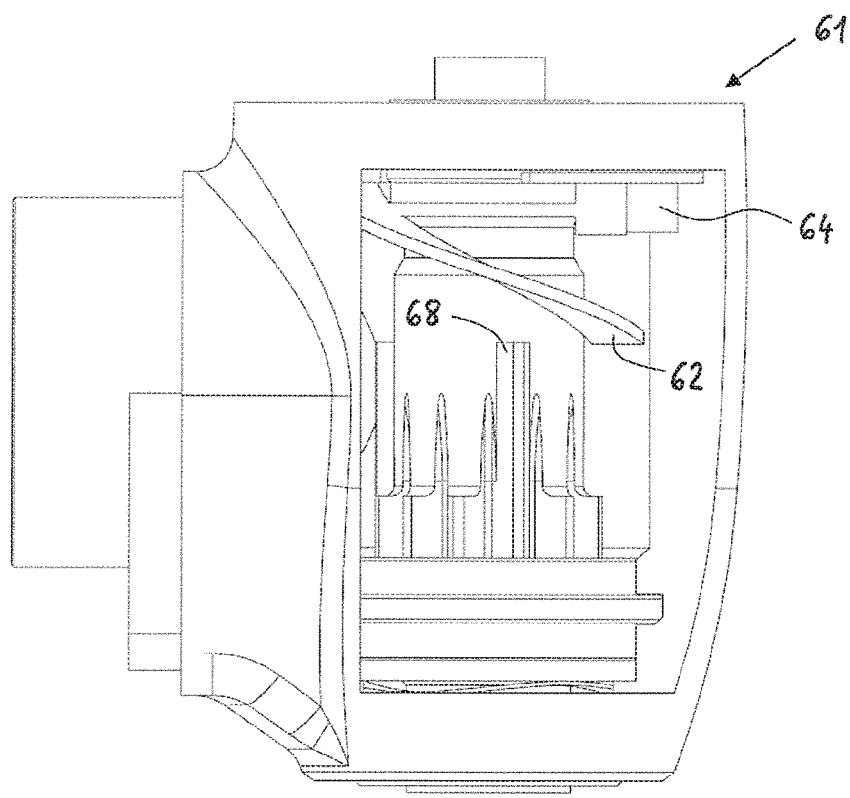
Figure 19:
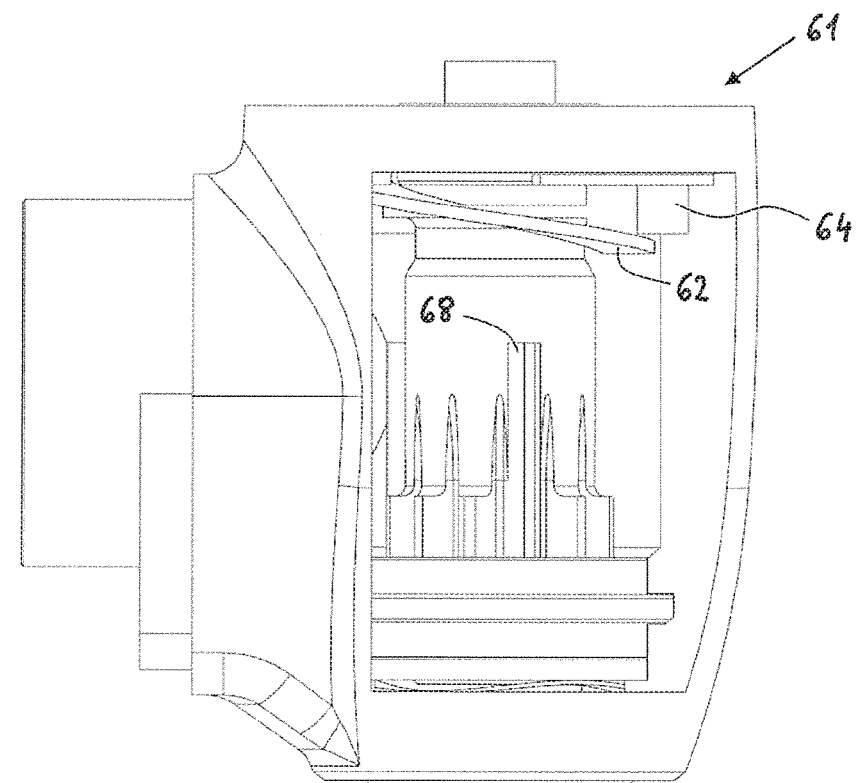

FIGS. 17-19 show a medical or dental instrument 61, preferably a handpiece and/or a front section or head section thereof. The instrument 61 comprises a temperature display device and/or a temperature-measuring device 60 for measuring the temperature in or on the instrument 61 or at least a part of the instrument 61. The temperature-measuring device 60 comprises a magnetic material 62, wherein at least one magnetic property of the magnetic material 62, preferably the magnetic flux density or the magnetic susceptibility, depends on the temperature and/or has a temperature-dependent course. The magnetic material 62 of the temperature-measuring device 60 is preferably designed such, that the magnetic property of the magnetic material 62, preferably the magnetic flux density or the magnetic susceptibility declines with an increase in temperature. The temperature-measuring device and/or the temperature display device 60 comprises a mechanical switching device 63, comprising the magnetic material 62. The switching device 63 comprises at least one magnetic element 64, in particular a permanent magnetic element, wherein the magnetic element 64 and the magnetic material 62 are designed to cooperate magnetically, preferably to optionally attract one another. It can also be seen from FIGS. 17-19 that the magnetic material 62 and the magnetic element 64 can be moved in relation to one another, wherein the magnetic element 64 is preferably essentially immovable in relation to the magnetic material 62 and/or at least a portion of the magnetic material 62 is movable in relation to the magnetic element 64. The magnetic material 62 has an elongated shape, preferably a bent shape, for example, a clip shape. The magnetic material 62 and the magnetic element 64 are prestressed resiliently in relation to one another; the magnetic material 62 in particular is designed as a spring clip or as a spring arm. Alternatively, the magnetic material 62 is part of a flexible or bendable element or of a spring element 65 or the magnetic material 62 is prestressed by a spring element 65.

The switching device 63 is designed to contact and/or to block a movable part 66 of the instrument 61, in particular a shaft 66A that can be put in motion, by a relative movement between the magnetic material 62 and the magnetic element 64. The moving part 66 is designed in particular as part of a drive device for driving a tool, preferably rotatably driving a tool, that can be connected to the instrument 61, and/or as part of a tool holder or a tool receptacle 67 and/or as a chucking or holding element for the tool. The tool holder 67 has a borehole 90 to receive a tool.

FIGS. 17 and 19 show the switching device 63 in a first switching state in which the at least one temperature-dependent magnetic property of the magnetic material 62, preferably the magnetic flux density or the magnetic susceptibility is increased. Therefore the magnetic material 62 is magnetically attracted by the magnetic element 64 and is moved in the direction of the magnetic element 64 because of its flexibility or bendability or because of the flexibility or bendability of the spring element 65, preferably until coming in contact with the magnetic element 64 and/or is moved away from the moving part 66, 66A of the instrument 61, in particular preventing contact with the moving part 66, 66A. The switching device 63 assumes this first switch state preferably up to a temperature of approximately 50° C.-60° C. The temperature of up to approximately 50° C.-60° C. occurs near the magnetic material, for example, in the interior of the instrument 61, preferably in the interior of the instrument head/handpiece head and/or on or near movable components of the instrument 61, for example, bearings or the tool holder 67.

If the temperature reaches or exceeds approximately 50° C.-60° C., the magnetic property of the magnetic material 62, preferably the magnetic flux density or the magnetic susceptibility and thus the magnetic attraction of the magnetic material 62 by the magnetic element 64 decrease such that the magnetic material 62 is released from the magnetic element 64 due to the prestress or spring action of the spring element 65 and/or moves away from the magnetic element 64 and moves in the direction of the moving part 66, 66A of the instrument 61 and contacts the moving part 66, 66A or at least an element 68 connected to it, for example, a projection, a protrusion, a nose or a strip (see FIGS. 18 and 20). This status corresponds to the second switching state of the switching device 63. Through this contact, the moving part 66, 66A is blocked or stopped in its movement by the magnetic material 62 and/or the spring element 65 or an acoustic signal is generated when the moving part 66, 66A moves in relation to the magnetic material 62 and/or the spring element 65. The switching device 63 is thus preferably designed like a ratchet.

FIGS. 17-19 additionally show: a shell or outer shell 61A of the instrument or handpiece 61; an instrument head or handpiece head 85 of the instrument or handpiece 61; a media-dispensing device 86 provided in or on the instrument head 85, in particular for dispensing water and/or air, wherein the media-dispensing device 86 preferably has one or more nozzles; a tool receptacle opening 87 provided on the instrument head 85 or on the outer shell 61A; bearing seats 88 for bearings for support, in particular rotational support, of the tool holder 67 or the movable part 66, in particular the shaft 66A; a gearwheel or pinion 89 on the moving part 66, in particular on the shaft 66A.

FIG. 21 shows the switching device 63 with a base 91, which is preferably bent or arc-shaped and essentially flat, on which the magnetic element 64, in particular the permanent magnetic element is provided via a protrusion or extension 92 of the magnetic element 64 serving as a magnet carrier. The spring element 65, which is preferably also bent or arc-shaped and comprises the magnetic material 62, or on which the magnetic material 62 is provided, is connected to the base 21. At least a part of the spring element 65 and/or of the magnetic material 62 is arranged outside of the plane in which the base 91 extends. A bore 93 in the base 91, in which a pin, for example, can be accommodated serves to provide rotationally fixed positioning and/or attachment of the switching device 63 in or on the instrument 61, in particular in the instrument head 85.

Figure 22:
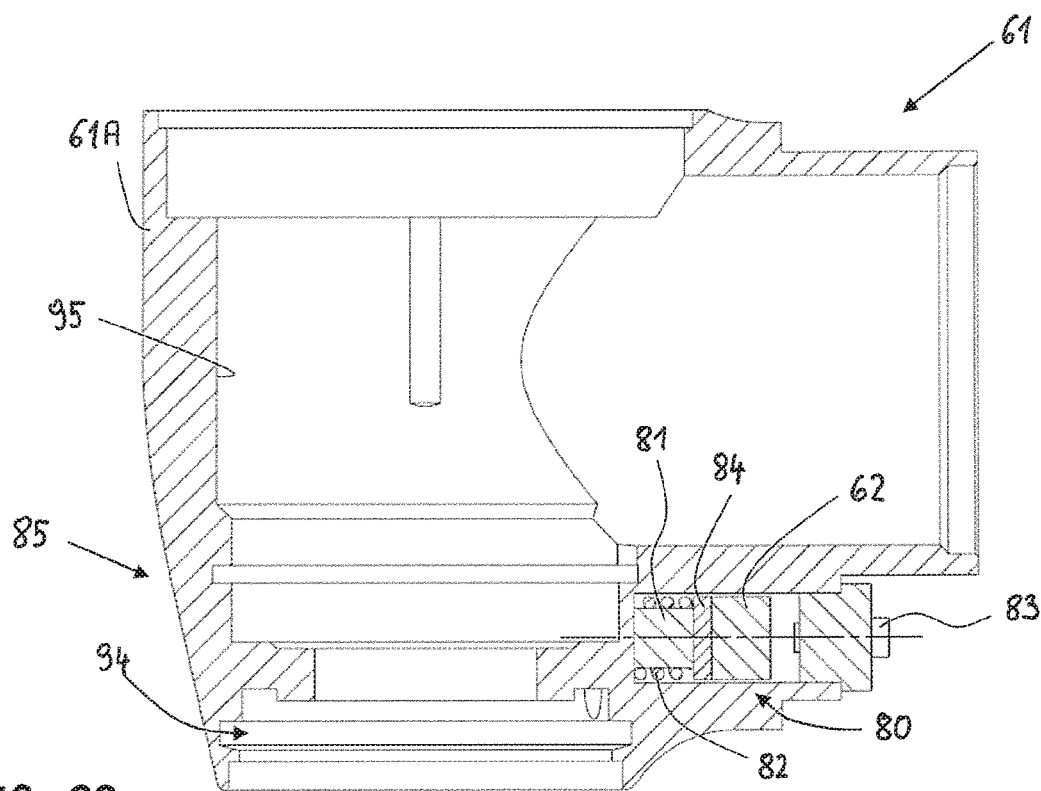
Figure 23:
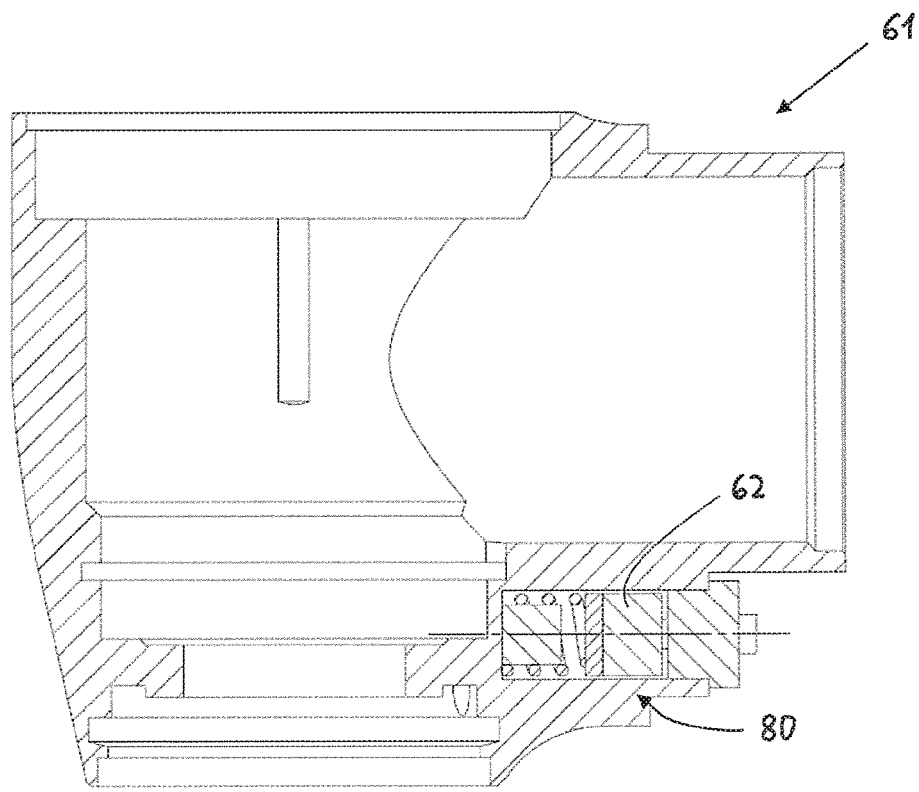

FIGS. 22, 23 show an alternative embodiment of a temperature-measuring device or in particular an electric or electromechanical switching device 80 or a medical or dental instrument 61, preferably a handpiece and/or a front section or head section 85 thereof. The switching device 80 comprises a magnetic element 81, preferably a permanent magnet, a magnetic material 62, a spring element 82, two electric contacts 83 (only one contact is discernible) and preferably a magnetic and/or electric insulator 84. In addition, a receptacle 95 for a media-dispensing device 86 is provided on the head section 85 or in the outer shell 61A. (see FIG. 17) and an interior 95 for receiving a drive element 66, a tool holder 67, a bearing or additional components can be seen.

The magnetic material 62 is movable in relation to the magnetic element 81 and in particular is prestressed by means of the spring element 82 with respect to the magnetic element 81. The magnetic material 62 may thus assume at least two switching positions, namely a first switching position in which it is spaced from the magnetic element 81 and contacts the two contacts 83 (see FIG. 23) and a second switching position in which it is arranged close to the magnetic element 81, preferably contacting it directly or indirectly, for example, by way of the insulator 84, and does not contact the two contacts 83 or is separated from them, for example, by an air gap (see FIG. 22).

The magnetic material 62 is designed as an electrically conductive material or switching element through which an electric or electronic circuit can be closed and opened. If the magnetic material 62 is electrically connected to the contacts 83 or if it contacts same (see FIG. 23), then the circuit is closed and electric energy can flow. As soon as the contact between the contacts 83 and the magnetic material 62 is severed, the circuit is opened and no electric energy can flow.

The magnetic material 62 assumes the first or second switching position again as a function of temperature and based on the variable magnetic property, preferably the magnetic flux density or the magnetic susceptibility, as described above in detail. Below a temperature of approximately 50° C.-60° C., the magnetic flux density of the magnetic material 62 is high so that it is attracted by the magnetic element 81 and the circuit is opened (see FIG. 22). If the temperature of approximately 50° C.-60° C. is exceeded, then the magnetic flux density of the magnetic material 62 is reduced such that the spring force exerted by the spring element 82 overcomes the magnetic force and moves the magnetic material 62 in the direction of the contacts 83 so that the circuit is closed (see FIG. 23).

FIGS. 24-29 show embodiments of temperature-measuring devices or switching devices 70A-70E with a magnetic material 62, wherein at least one magnetic property of the magnetic material 62, preferably the magnetic flux density or the magnetic susceptibility is dependent on the temperature and/or has a temperature-dependent course. The switching devices 70A-70E are part of a temperature display device and/or a temperature-measuring device for measuring the temperature in or on at least a part of a medical or dental instrument 61, preferably a handpiece. The switching devices 70A-70E are designed in particular as electric or electromechanical switching devices.

The fundamental design is the same with all switching devices 70A-70E and is described as follows: the switching devices 70A-70E have two magnetic elements 71A, 71B spaced a distance apart from one another, in particular permanent magnet elements, a first electric conductor 72A and a second electric conductor 72B, preferably made of a ferromagnetic material and at least one component of a magnetic material 62, at least one magnetic property of which, preferably the magnetic flux density or the magnetic susceptibility, is dependent on temperature or has a temperature-dependent course. In contrast with the embodiments described above, the magnetic elements 71A, 71B and the magnetic material 62 of the switching devices 70A-70E are immovable or stationary in relation to one another.

The magnetic material 62 is arranged between the magnetic elements 71A, 71B so that the magnetic material 62 and the magnetic elements 71A, 71B form a receptacle 73 for the electric conductors 72A, 72B, in particular for their (free) ends. The component of the magnetic material 62 is designed, for example, as a shell, in particular as a hollow or hollow cylindrical shell or as a curved shape, for example, a shell-shaped element or a half-shell. The magnetic elements 71A, 71B are designed as plates or disks, for example, or as plate-shaped or disk-shaped elements. The electric conductors 72A, 72B enter into the receptacle 73 through one or more openings 74, for example, through a bore or a slot-shaped opening in the magnetic elements 71A, 71B. According to the figures each magnetic element 71A, 71B has an opening 74 for the passage of one conductor 72A, 72B each.

The electric conductors 72A, 72B are arranged in such a way that at least one section, in particular their free ends are situated side by side or adjacent to one another. The electric conductors 72A, 72B, in particular their free ends are designed to be flexible, at least slightly, so that they are movable in relation to one another, in particular being movable toward one another. The electric conductors 72A, 72B are additionally part of an electric or electronic circuit having at least one electric current source.

In addition, the switching devices 70A-70E preferably comprise a housing 75 in which a east a portion of the electric conductors 72A, 72B, in particular their free ends are accommodated or housed. The housing 75 is preferably made of electrically nonconductive material, for example, glass. The housing 75 has at least two openings or passages for the electric conductors 72A, 72B. The housing 75 is preferably filled with an inert gas or an inert gas mixture, for example, with nitrogen, or it contains a vacuum. In FIGS. 24-26 and 28, 29 the housing is arranged in the receptacle 73 and surrounds only the ends of the electric conductors 72A, 72B. Alternatively, the housing 75 may be designed so that it encloses additional components, for example, at least one of the magnetic elements 71A, 71B and/or the magnetic material 62 (see FIG. 27).

Figure 29:
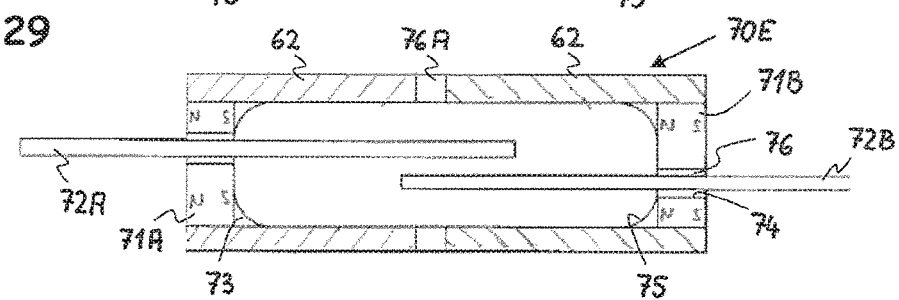

Finally at least one electric and/or magnetic insulator 76 is preferably provided on the switching devices 70A-70E, in particular between the several, in particular two, magnetic elements 71A, 71B and the two electric conductors 72A, 72B and/or between the several, in particular two, magnetic elements 71A, 71B and the magnetic material 62 and/or between separate sections of the magnetic material 62 (see FIG. 29). The at least one insulator 76 serves to electrically insulate the electric conductors 72A, 72B and/or to shape, guide or concentrate the magnetic fields or magnetic field lines formed on the switching devices 70A-70E. The insulator 76 comprises, for example, an air gap and/or a ceramic material and/or a plastic. The insulator 76 is designed for example, as a disk shaped or plate-shaped element.

Figure 24:
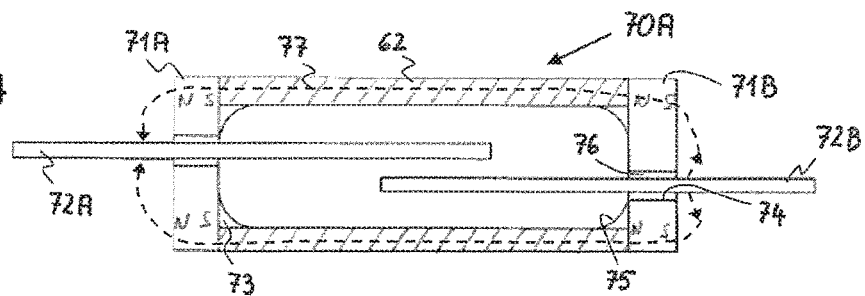
FIGS. 24-29 show different embodiments of a switching device having a magnetic material, wherein at least one magnetic property of the magnetic material, preferably the magnetic flux density or the magnetic susceptibility, is a function of temperature and/or has a temperature-dependent course, wherein the switching device is preferably part of a temperature-measuring device for measuring the temperature in or at the handpiece or at least of a part of a medical or dental instrument, preferably a handpiece.
Figure 25:
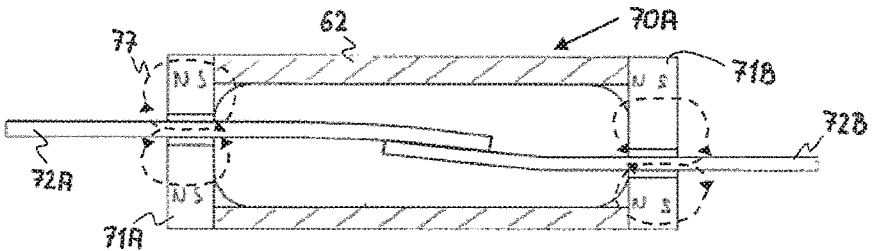

The functioning of the switching devices 70A-70E can be seen in FIGS. 24 and 25 on the basis of the course of the magnetic field and/or the magnetic field lines that are shown schematically. FIG. 24 shows the course of the magnetic field lines 77 beneath the switching temperature of the magnetic material 62, preferably a temperature in the range of approximately 50° C.-60° C. The magnetic material 62 has a high magnetic flux density or ferromagnetic properties so that the magnetic field lines 77 run between the two magnetic elements 71A, 71B (longitudinally) through the magnetic material 62. Thus there is a single magnetic field permeating the entire switching devices 70A-70E in which field the electric conductors 72A, 72B, in particular their free ends are separated from one another. Thus the electric or electronic circuit of which the electric conductors 72A, 72B are a part is open and no electric energy can flow through the circuit.

If the temperature of the magnetic material 62 exceeds the switching temperature, the magnetic flux density or the ferromagnetic properties of the magnetic material 62 are reduced to such an extent that the course of the magnetic field lines 77 resembles the schematic diagram in FIG. 25. The electric conductors 72A, 72B, in particular their free ends thus have different magnetic polarities and attract one another until they come in contact because of their flexibility. Thus the electric or electronic circuit of which the electric conductors 72A, 72B are a part is closed and electric energy can flow through the circuit.

Figure 26:
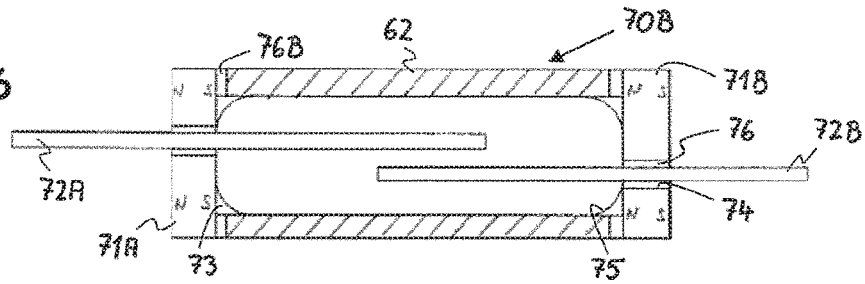
Figure 27:
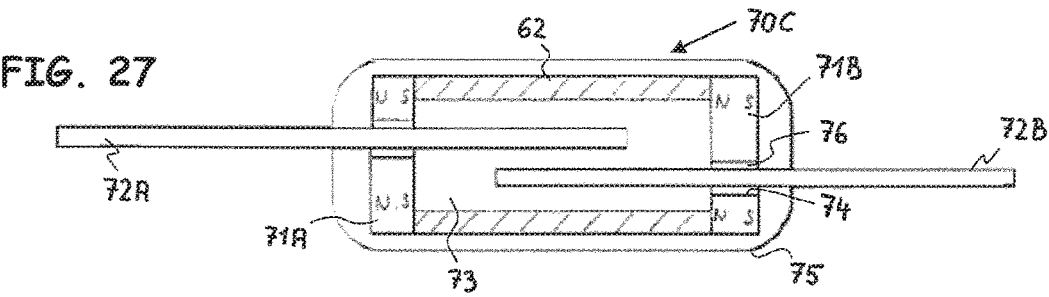
Figure 28:
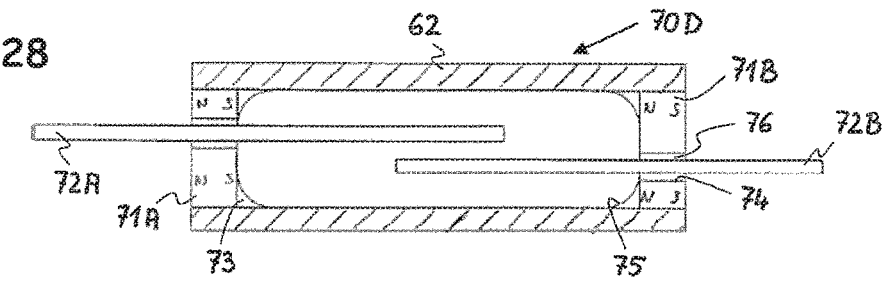

The switching devices 70B-70E of FIGS. 26-29 exhibit the following variants: FIG. 26 shows an additional electric and/or magnetic insulator 76B that is provided between the magnetic elements 71A, 71B and the magnetic material 62. FIG. 27 shows a housing 75, which holds not only the electric conductor 72A, 72B but also the magnetic elements 71A, 71B, the magnetic material 62 and the insulator 76. In FIG. 28 the magnetic material 62 protrudes beyond the magnetic elements 71A, 71B or encloses the magnetic elements 71A, 71B on their outside or their lateral surface. FIG. 29 shows another electric and/or magnetic insulator 76A on the magnetic material 62, which is designed in two parts in particular. The insulator 76A is provided in particular in the area of the free ends of the electric conductors 72A, 72B to channel or concentrate the magnetic field or the magnetic field lines in the area of the free ends in the direction of the electric conductors 72A, 72B.

Because of the limited space situation in the interior of many medical instruments 61, in particular dental handpieces, the diameter of the switching devices 70A-70E amounts to less than 3.0 mm, preferably less than 2.0 mm, in particular approximately 1.5 mm, and the longitudinal extent of the switching devices 70A-70E amounts to less than 5.0 mm, preferably less than 4.0 mm, in particular approximately 2.5 mm.

The electric or electronic circuits mentioned above, of which the electric conductors 72A, 72B or the switching devices 70A-70E or the electric contacts 83 or the switching device 80 are a part of are preferably designed identically as shown in FIGS. 14-16. The temperature-measuring device 34 described in conjunction with FIGS. 14-16 is formed accordingly by a switching device 70A-70E or 80. All the other components of the circuit, in particular the power supply and the temperature display (light source, light-emitting diode) may preferably be designed as shown in FIGS. 14-16 and as described in the respective description. Alternatively, only the switching devices 70A-70E or 80 are arranged in or on the instrument 61 or the handpiece and all other components of the circuit are provided outside of the instrument 61 or the handpiece, in particular in a regulating and/or control unit and/or a power supply unit, which is or can be connected to the instrument 61 or the handpiece. In addition, all embodiments depicted and described in conjunction with FIGS. 14-16 with respect to the electric current source of the circuit, the arrangement of the temperature-measuring device/switching devices 70A-70E or 80 and the arrangement and design of the display, can be applied or transferred to the switching devices 70A-70E or 80 or an instrument 61 or a handpiece having such a switching device 70A-70E.

The magnetic material 62 described in the embodiments above, of which at least one magnetic property, preferably the magnetic flux density or the magnetic susceptibility depends on the temperature and/or has a temperature-dependent course, comprises, for example, a metallic compound, in particular a metallic alloy, for example, an alloy containing nickel and iron, alloys of non-ferromagnetic elements (for example, Heusler alloys) or an alloy containing nickel and copper (for example, Monel alloy). For example, one suitable alloy is distributed by the company Vacuumschmelze GmbH & Co. KG, Hanau, Germany under the name Thermoflux®, in particular Thermoflux® 55/100-G.

All the magnetic materials 62 preferably have in common that their ferromagnetism or their ferromagnetic property, in particular the strength of their permanent magnetic field is reduced with an increase in temperature and that they have paramagnetic properties in particular on reaching or exceeding a predetermined temperature (switching temperature). If the temperature drops below the switching temperature, the magnetic material 62 again has ferromagnetic properties. The change between ferromagnetic and paramagnetic properties based on a change in temperature may take place as often as desired.

For the present application, i.e., for the temperature measurement, monitoring and/or display of a medical or dental instrument 61, in particular a handpiece, the switching temperature at which there is in particular a change between ferromagnetic and paramagnetic properties is approximately between 45° C. and 65° C., preferably approximately between 50° C. and 60° C., in particular preferably approximately between 52° C. and 56° C.

The electric or electronic circuits described above or the switching devices 70A-70E or 80 may optionally be constructed so, that on reaching or exceeding the switching temperature, either the switching circuit is opened so that no electric energy flows in the circuit, or the circuit is closed so that electric energy can flow in the circuit.

The invention is not limited to the embodiments described here, but instead includes all embodiments, which apply or include the basic appropriate function principal of the invention. Thus in particular the position of all the temperature measuring devices described is variable in the instrument or handpiece and is not limited exclusively to the head part. In general, the temperature device may be arranged at any location in the instrument or handpiece, in particular where heat sources are positioned in the instrument or handpiece or where an outside surface of the instrument or handpiece gets particularly warm.

In addition, all the features of the all the embodiments described and depicted here may be combined with one another. In particular temperature sensors or specific methods of temperature measurement which are described with reference to an embodiment can also be implemented in handpieces of other embodiments. For example, it is also possible to provide different sensors in a handpiece 1, 30, for example, an infrared sensor 9 and a thermocouple 13. The measurement signals emitted by the different sensors may be analyzed either separately from one another and/or combined for a shared combined analysis, for example, for forming a temperature average or a weighted temperature value, preferably by a control, regulating and/or power supply unit 23.

What is claimed is:

1. A medical handpiece, comprising
    a handpiece head having an outer shell defining an inner volume,
    a tool holder device for releasably holding a tool that can be connected to the handpiece, wherein the tool holder device is moveably arranged in the inner volume,
    at least one bearing unit operatively connected to the tool holder device to moveably support the tool holder device, wherein the at least one bearing unit is arranged in the inner volume,
    a drive device for setting in motion a tool that can be connected to the tool holder device,
    an electrical temperature sensor of a temperature-measuring device for measuring a temperature of the at least one bearing unit, wherein the electrical temperature sensor is arranged in the inner volume of the handpiece head, and wherein the electrical temperature sensor comprises an electric resistor having a material whose electric resistance or dynamic resistance is variable as a function of temperature, and
    an electric and signal line connecting the temperature sensor of the temperature-measuring device to a unit having
        (i) a current or voltage source to supply a constant electric measuring current to the temperature sensor, wherein a temperature measuring signal comprises a value of the electric measuring current sent from the current or voltage source over the temperature sensor or a change in the value of the electric measuring current sent from the current or voltage source over the temperature sensor, which is indicative of the temperature of the at least one bearing unit, and
        (ii) an evaluation unit for evaluating the temperature measuring signal, and a regulating or control unit for temperature-dependent regulation or control of the medical handpiece based on the temperature measuring signal,
    wherein the electric and signal line extends out of the handpiece head to connect to the unit.

2. The medical handpiece according to claim 1, wherein the electrical temperature sensor is arranged in a partial space of the inner volume, wherein said partial space is defined on a first side by the at least one bearing unit.

3. The medical handpiece according to claim 2, wherein the at least one bearing unit is a first bearing unit and wherein the medical handpiece comprises a second bearing unit operatively connected to the tool holder device to moveably support the tool holder device and at a distance from the first bearing unit, wherein the partial space which accommodates the temperature sensor is arranged between the first and the second bearing unit.

4. The medical handpiece according to claim 2, wherein the at least one bearing unit is a first bearing unit and wherein the medical handpiece comprises a second bearing unit operatively connected to the tool holder device to moveably support the tool holder device and at a distance from the first bearing unit, wherein the partial space is defined on a second side by the second bearing unit.

5. The medical handpiece according to claim 1, wherein the at least one bearing unit is a first bearing unit, wherein the medical handpiece comprises a second bearing unit operatively connected to the tool holder device to moveably support the tool holder device, wherein the second bearing unit is arranged in the inner volume, and wherein the electrical temperature sensor measures the temperature of the first and second bearing unit.

6. The medical handpiece according to claim 1, wherein the electrical temperature sensor of the temperature-measuring device is configured to receive electromagnetic radiation or thermal radiation of a plurality of parts arranged in the outer shell of the handpiece head to determine an average temperature value of the plurality of parts.

7. The medical handpiece according to claim 1, wherein the electrical temperature sensor of the temperature-measuring device is designed to measure the temperature of the inner volume defined by the outer shell of the handpiece head and/or of a partial space of the inner volume that can be heated by at least one of: the at least one bearing unit to moveably support the tool holder device, the tool holder device and at least one further heat source arranged in the outer shell of the handpiece head.

8. The medical handpiece according to claim 7, wherein the further heat source comprises at least one of: a gear, a tool-releasing device, an illuminating device, a heating element for media, an electrical or electronic component.

9. The medical handpiece according to claim 1, wherein the material whose electric resistance or dynamic resistance is variable as a function of temperature comprises at least one of: a ceramic, and a doped semiconductor.

10. The medical handpiece according to claim 1, further comprising an electrical switching device which is electrically connected to the temperature-measuring device and to a signal device to receive the temperature-measuring signal supplied by the temperature-measuring device and to switch the signal device between at least one first signal condition and one second signal condition, which is different from the first signal condition, when the temperature-measuring signal reaches, exceeds or falls below a limit value.

11. The medical handpiece according to claim 10, wherein the first signal condition and the second signal condition comprise at least one of: a visually perceptible signal, an acoustically perceptible signal and a tactilely perceptible signal.

12. The medical handpiece according to claim 1, wherein the electrical temperature sensor of the temperature-measuring device is at least one of: arranged on an inside of a jacket of the outer shell of the head extending between an actuating element for the tool holder and a tool opening for receiving the tool; arranged in a partial space of the inner volume bordered by the outer shell of the head, the tool holder, the at least one bearing unit which is a first bearing unit and a second bearing unit supporting the tool holder; arranged in the vicinity of the at least one bearing unit which is a first bearing unit that is closer to a tool opening for receiving the tool than a second bearing unit supporting the tool holder.

13. A medical handpiece, comprising
a handpiece head having an outer shell defining an inner volume,
a tool holder device for releasably holding a tool that can be connected to the handpiece, wherein the tool holder device is moveably arranged in the inner volume,
at least one bearing unit operatively connected to the tool holder device to moveably support the tool holder device, wherein the at least one bearing unit is arranged in the inner volume,
a drive device for setting in motion a tool that can be connected to the tool holder device,
an electrical temperature sensor of a temperature-measuring device for measuring a temperature of at least one heat source of the medical handpiece, wherein the electrical temperature sensor is mounted on the at least one heat source in the inner volume of the handpiece head, and
an electric and signal line connecting the temperature sensor of the temperature-measuring device to a unit comprising an evaluation unit for evaluating measured signals of the temperature-measuring device indicative of the temperature of the at least one heat source of the medical handpiece, and a regulating or control unit for temperature-dependent regulation or control of the medical handpiece; wherein the electric and signal line extends out of the handpiece head to connect to the unit.

14. The medical handpiece according to claim 13, wherein the at least one heat source is a first heat source, and wherein the electrical temperature sensor is further configured to measure the temperature of at least a second heat source arranged in the inner volume of the handpiece head.

15. The medical handpiece according to claim 13, wherein the at least one heat source comprises the at least one bearing unit operatively connected to the tool holder device to moveably support the tool holder.

16. The medical handpiece according to claim 13, wherein the electrical temperature electrical sensor of the temperature-measuring device comprises at least one of: a thermocouple designed to supply a thermoelectric voltage signal for the measurement of the temperature; a material whose electric resistance or dynamic resistance is variable as a function of temperature; or an electric resistor.

17. The medical handpiece according to claim 13, wherein the medical handpiece is coupled to a display unit for displaying the measured or determined temperature value or a temperature limit value.

18. A medical handpiece, comprising
a handpiece head having an outer shell defining an inner volume,
a tool holder device for releasably holding a tool that can be connected to the handpiece, wherein the tool holder device is moveably arranged in the inner volume and extends along a longitudinal axis,
a first bearing unit operatively connected to the tool holder device to moveably support the tool holder device, wherein the first bearing unit is arranged in the inner volume of the handpiece head,
a second bearing unit operatively connected to the tool holder device to moveably support the tool holder device, wherein the second bearing unit is arranged in the inner volume of the handpiece head at a distance from the first bearing unit,
a drive device for setting in motion a tool that can be connected to the tool holder device,
a space arranged in the handpiece head extending around the tool holder device and along the longitudinal axis of the tool holder device and accommodating the first bearing unit, the second bearing unit and at least a portion of the drive device, and
an electrical temperature sensor of a temperature-measuring device for measuring a temperature of the first bearing unit and the second bearing unit and an electric and signal line extending out of the handpiece head to connect to a unit, wherein
the electrical temperature sensor is disposed in said space in the handpiece head.

19. The medical handpiece according to claim 18, wherein the electrical temperature sensor of the temperature-measuring device is configured to measure the temperature of at least one additional heat source in the medical handpiece head.

20. The medical handpiece according to claim 19, wherein the electrical temperature sensor is configured to determine an average or common temperature value of the first bearing unit and the second bearing unit and the at least one additional heat source.

21. The medical handpiece according to claim 18, wherein at least a portion of the space is defined by an inner wall of the outer shell of the handpiece head.

22. The medical handpiece according to claim 19, wherein the at least one additional heat source comprises at least one of: an illuminating device; or an electrical component.

23. The medical handpiece according to claim 18, wherein the electrical temperature sensor is arranged on the first bearing unit or the second bearing unit.

* * * * *